(12) United States Patent
Bataille et al.

(10) Patent No.: US 9,982,247 B2
(45) Date of Patent: May 29, 2018

(54) METHOD FOR PURIFYING TRANSGENIC FACTOR VII/VIIA

(71) Applicant: LABORATOIRE FRANCAIS DU FRACTIONNEMENT ET DES BIOTECHNOLOGIES, Les Ulis (FR)

(72) Inventors: Damien Bataille, Ormoy (FR); Michel Nogre, Vanves (FR); Abdessatar Sami Chtourou, Elancourt (FR)

(73) Assignee: LABORATOIRE FRANCAIS DU FRACTIONNEMENT ET DES BIOTECHNOLOGIES, Les Ulis (FR)

( * ) Notice: Subject to any disclaimer, the term of this patent is extended or adjusted under 35 U.S.C. 154(b) by 0 days. days.

(21) Appl. No.: 14/415,254

(22) PCT Filed: Jul. 18, 2013

(86) PCT No.: PCT/EP2013/065205
§ 371 (c)(1),
(2) Date: Jan. 16, 2015

(87) PCT Pub. No.: WO2014/013024
PCT Pub. Date: Jan. 23, 2014

(65) Prior Publication Data
US 2015/0175983 A1    Jun. 25, 2015

(30) Foreign Application Priority Data
Jul. 19, 2012    (EP) .................................... 12305882

(51) Int. Cl.
C12N 9/24        (2006.01)
C07K 16/36       (2006.01)
C12N 9/64        (2006.01)

(52) U.S. Cl.
CPC ............... *C12N 9/24* (2013.01); *C07K 16/36* (2013.01); *C12N 9/6437* (2013.01); *C07K 2317/22* (2013.01); *C07K 2317/569* (2013.01); *C12Y 304/21021* (2013.01)

(58) Field of Classification Search
None
See application file for complete search history.

(56) References Cited

U.S. PATENT DOCUMENTS

| | | |
|---|---|---|
| 4,784,950 A | 11/1988 | Hagen et al. |
| 5,344,918 A | 9/1994 | Dazey et al. |
| 5,759,808 A | 6/1998 | Casterman et al. |
| 5,800,988 A | 9/1998 | Casterman et al. |
| 5,840,526 A | 11/1998 | Casterman et al. |
| 5,874,541 A | 2/1999 | Casterman et al. |
| 6,015,695 A | 1/2000 | Casterman et al. |
| 6,268,487 B1 | 7/2001 | Kutzko et al. |
| 6,838,254 B1* | 1/2005 | Hamers ............... C07K 16/00 424/130.1 |
| 7,214,319 B2 | 5/2007 | Yen et al. |
| 7,794,981 B2* | 9/2010 | Hamers ............... C07K 16/00 435/70.21 |
| 8,492,524 B2 | 7/2013 | Lejars et al. |
| 9,029,316 B2 | 5/2015 | Bardat et al. |
| 2004/0251202 A1 | 12/2004 | Yen et al. |
| 2005/0130266 A1 | 6/2005 | Hamers et al. |
| 2009/0281283 A1 | 11/2009 | Lejars et al. |
| 2009/0311239 A1 | 12/2009 | Chtourou et al. |
| 2010/0047428 A1 | 2/2010 | Lejars et al. |
| 2011/0059510 A1 | 3/2011 | Ripoll |
| 2011/0104142 A1 | 5/2011 | Rischel et al. |
| 2012/0087908 A1 | 4/2012 | Bardat et al. |
| 2012/0122179 A1 | 5/2012 | Perret et al. |
| 2013/0295646 A1 | 11/2013 | Lejars et al. |
| 2014/0093491 A1 | 4/2014 | Chtourou et al. |
| 2015/0216951 A1 | 8/2015 | Bardat et al. |

FOREIGN PATENT DOCUMENTS

| | | |
|---|---|---|
| CN | 102161701 | 8/2011 |
| EP | 0346241 | 12/1989 |
| EP | 0527063 | 2/1993 |
| EP | 0547932 | 6/1993 |
| FR | 2947181 | 12/2010 |
| JP | H08508264 A | 9/1996 |
| JP | 2010-514746 A | 5/2010 |
| TW | I268933 | 12/2006 |
| WO | 94-04678 | 3/1994 |
| WO | 94/22905 A1 | 10/1994 |
| WO | 94-25591 | 11/1994 |
| WO | 2007-138198 | 12/2007 |
| WO | 2007-138199 | 12/2007 |
| WO | 2008-099077 | 8/2008 |
| WO | 2009-141418 | 11/2009 |
| WO | 2010/094901 A1 | 8/2010 |

OTHER PUBLICATIONS

Detmers et al. (Chromatography, Feb. 1, 2010).*
European Search Report, dated Dec. 17, 2012; Application No. 12 30 5882.
Hagen et al., "Characterization of a cDNA coding for human factor VII," Proc. Natl. Acad. Sci. USA, vol. 83, pp. 2412-2416, Apr. 1986.
Kaplan et al., "Laboratory techniques in rabies," Fourth Edition, World Health Organization, 1986, pp. 1-65.
Ruiz et al., "Expression and Purification of Recombinant Rabbit Factor VII," Thrombosis Research 98 (2000), pp. 203-211.
International Search Report, dated Sep. 20, 2013; Application No. PCT/EP2013/065205.
English translation of Taiwan Examination Report from corresponding Taiwan Application No. 102125684.
Third party observation, dated Jun. 23, 2016, from corresponding European Application No. 13739975.
Detmers, F. et al., "Novel Affinity Ligands for Bioprocessing," Biotechnology, 2007.

(Continued)

Primary Examiner — Hope Robinson
(74) Attorney, Agent, or Firm — Young & Thompson

(57) ABSTRACT

An anti-Factor VII affinity ligand that is particularly useful for purifying recombinant human activated Factor VII from transgenic sources. The affinity ligand combined with other orthogonal chromatographic steps allows the preparation of a highly purified FVII solution fully activated free of aggregates with a low percentage of degraded or oxidized FVII forms.

17 Claims, 5 Drawing Sheets

(56) References Cited

OTHER PUBLICATIONS

Figure 1:
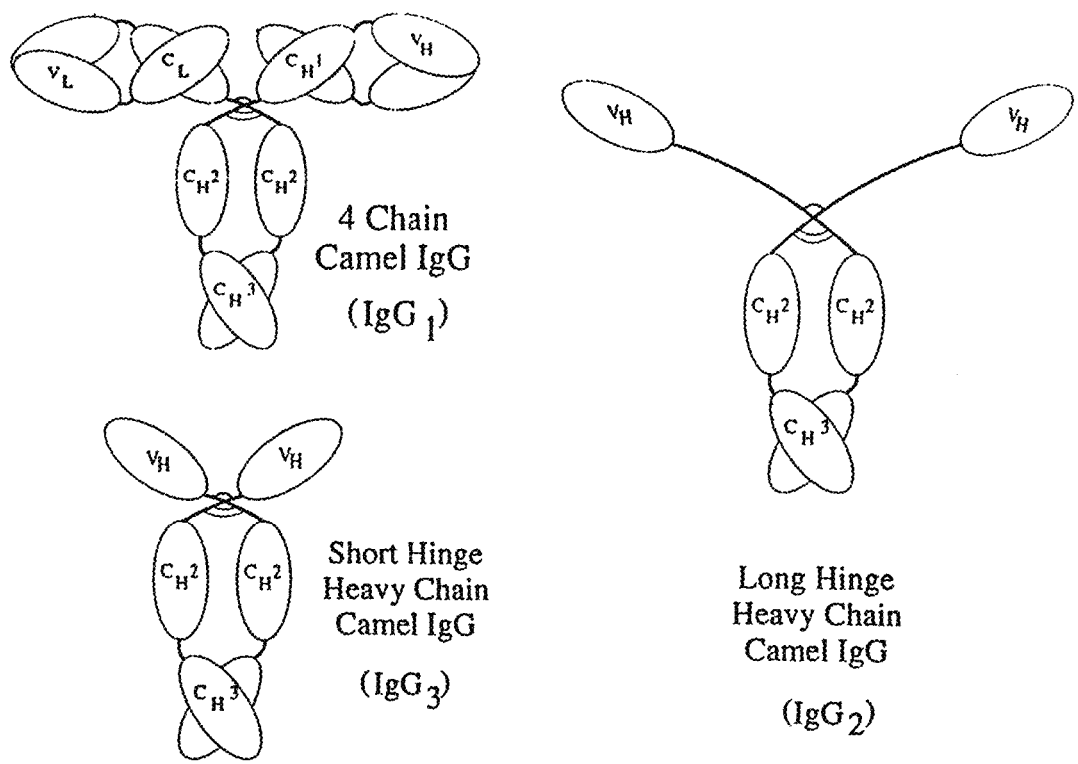

Macdonald G., "BAC to develop Factor VIIa purification ligand for LFB," Jun. 2, 2008.

Japanese Office Action, dated Jun. 20, 2016, from corresponding Japanese Application No. 2015-522099.

Singapore Written Opinion, dated Jul. 22, 2016, from corresponding Singapore Application No. 11201500254P.

Klooster, R. et al., "Improved anti-19G and HSA affinity ligands: Clinical application of VHH antibody technology," J. Immunol. Methods, May 2007, vol. 324, No. 1-2, pp. 1-12.

English translation of Chinese Office Action from corresponding Chinese Application No. 201380048473.2.

Youhong S. et al., "Research Progress on Immunological Therapy Application of Single Domain Antibodies Derived from Camel," Biotechnology Bulletin, 2010, Issue 6, pp. 27-32.

\* cited by examiner

METHOD FOR PURIFYING TRANSGENIC FACTOR VII/VIIA

FIELD OF THE INVENTION

The present invention relates to an anti-Factor VII affinity ligand that is particularly useful for purifying recombinant human activated Factor VII from transgenic sources. The affinity ligand combined with other orthogonal chromatographic steps allows the preparation of a highly purified FVII solution fully activated free of aggregates with a low percentage of degraded or oxidized FVII forms.

BACKGROUND OF THE INVENTION

Factor VII (FVII) is a vitamin K dependent glycoprotein which in its activated form (FVIIa) takes part in the coagulation process activating the Factor X and the Factor IX in the presence of calcium and of tissue factor. FVII is secreted in form of a single peptide chain of 406 residues, with a molecular weight of about 50 kDa. The FVII contains four distinctive structural domains: the N-terminal gamma-carboxylic domain (Gla), two "epidermal growth factor (EGF)-like" domains, and a serine protease domain. The activation of the FVII into FVIIa is characterized by the cleavage of the Arg152-Ile153 domain (Arginine 152-Isoleucine 153) linkage. The FVIIa is, therefore, a compound with a light chain of 152 amino acids with a molecular weight of about 20 kDa, and with a heavy chain of 254 aminoacids with a molecular weight of about 30 kDa linked one to another with a single disulfide bridge (Cys135-Cys262).

The plasma FVIIa contains several post-translational modifications: the first ten glutamic acids are [gamma]-carboxylated, Asp63 is partially hydroxylated, Ser52 (Serine 52) and Ser60 (Serine 60) are 0-glycosylated and carry the Glucose (Xylose)0-2 and Fucose patterns, respectively, Asn145 (Asparagine 145) and Asn322 (Asparagine 322) are N-glycosylated mainly by biantennary bisialylated complex structures.

FVII is used for the treatment of patients suffering from hemophilia, showing a deficiency of Factor VIII (type A hemophilia) or of Factor IX (type B hemophilia), as of patients showing other deficiencies of coagulation factors, for example, a congenital deficiency of FVII. It is, therefore, necessary that concentrates of injectable FVIIa be available.

The most ancient method for obtaining FVIIa concentrates consisted in the purification of FVIIa from plasma proteins resulting from plasma fractionation. For that purpose, EP 0 346 241 describes the preparation of a FVIIa-enriched fraction, obtained after adsorption and then elution of a secondary product of the fractionation of plasma proteins containing FVII and FVIIa and other proteins such as Factors IX (FIX), X (FX) and II (FII), particularly the pre-eluate of PPSB (P=prothrombin or FII, P=proconvertin or FVII, S=Stuart Factor or FX and B=antihemophilic Factor B or FIX). The drawback of this process is that the obtained FVII still contains some traces of the other coagulation factors.

Likewise, document EP 0 547 932 describes a manufacturing process of a high purity FVIIa concentrate substantially free of vitamin-K-dependent factors and of FVIII. The FVII obtained by this process, in spite of its purity, shows a residual thrombogenic activity.

Generally speaking, one of major drawbacks of these processes is that they yield only small amounts of products. It is, moreover, still difficult to obtain a product entirely free of other proteins present in the plasma. Finally, although a number of precautions are being implemented at every stage of the preparation of plasma coagulation factors in order to ensure their viral and bacterial safety (follow-up of blood donors, tests for detecting of known viral and bacterial contaminants, stringent purification and virus inactivating treatments in order to reduce as far as possible the hazard of transmission of blood-born pathogenic agents), nevertheless, all risks of contamination with pathogenic agents are not excluded. In addition, the appearance of a new variant of the Creutzfeldt-Jakob disease gave rise to fears of transmission of unconventional pathogenic agents by blood products. Moreover, the volume of plasma collected from donors remains limited.

Therefore, since the 1980s, the DNA encoding the human Factor VII was isolated (Hagen et al. Proc. Natl. Acad. Sci., 1986, 83(8):2412-6) and expressed in various expression systems.

Various processes for the purification of recombinant Factor VII have further been described (see e.g. WO2009/141418). Currently recombinant Factor VII polypeptides are typically purified by one or two different multi-step processes, either employing exclusively chromatography on conventional resins, or including affinity chromatography employing an affinity resin with protein ligands.

Recombinant Factor VII may be produced from fermentation batches, or from transgenic mammals. In particular compositions of FVII produced in the mammary glands of female rabbit are described, e.g. in patent application WO2007/138199. The FVII produced in the milk by transgenic mammals can then be purified from milk e.g. by tangential filtration and chromatography, or by calcium precipitation followed by several chromatography steps.

However the available purification methods are not devoid of drawbacks. Especially native proteins from the transgenic mammal, and in particular native Factor VII from the transgenic mammal, might still be present, which would trigger immunogenicity upon administration to a human patient.

SUMMARY OF THE INVENTION

An object of the invention is a method for purifying transgenic Factor VII (TgFVII) and/or transgenic activated Factor VII (TgFVIIa) from a source biological material, comprising a step of affinity chromatography, comprising the steps of:

(a) contacting a source biological material containing TgFVII and/or TgFVIIa with a ligand which is specific to TgFVII and/or TgFVIIa, under conditions allowing the TgFVII and/or TgFVIIa to bind the ligand, and (b) recovering TgFVII and/or TgFVIIa by disrupting in a non destructive way the interaction with said ligand.

In an embodiment of the invention, the ligand is an antigen-binding protein directed to at least one TgFVII and/or TgFVIIa epitope, or a functional fragment or derivative thereof. Preferably, the ligand comprises two heavy polypeptide chains forming two complete antigen binding sites and is devoid of light polypeptide chains, and is derived from heavy immunoglobulin chains of Camelidae.

In an embodiment, the method of the invention is such that step (b) comprises at least one washing step for removing the unbound material before eluting TgFVII or TgFVIIa from the ligand, and further optionally comprises a second washing step for removing contaminants bound on the resin and having an affinity weaker than TgFVII or TgFVIIa In an embodiment of the invention, the source biological material used for purifying TgFVII or TgFVIIa is obtained from a transgenic animal producing TgFVII and/or TgFVIIa. Preferably, the animal is a mammal female, and preferably a rabbit female, and the source biological material is milk.

In an embodiment, the method of the invention further comprises the preliminary steps, before step (a), of collecting and clarifying milk. Preferably, the milk clarification step is performed by citrate salt addition followed by filtration.

In an embodiment, the method of the invention further comprises a step c) of chromatographic purification of the eluted TgFVII and/or TgFVIIa on an ion exchanger, and preferably on an anion exchanger, under conditions wherein TgFVII and/or TgFVIIa are retained on the ion exchanger. This step is preferably dedicated to TgFVII activation and to TgFVII and/or TgFVIIa polishing.

In an embodiment, the method of the invention further comprises a step d) of chromatographic separation of the eluted TgFVII and/or TgFVIIa on a pseudo-affinity resin, and preferably on hydroxyapatite, under conditions wherein TgFVII and/or TgFVIIa are retained on the pseudo-affinity resin. This step is preferably dedicated to TgFVII and/or TgFVIIa polishing and to the control of TgFVII and/or TgFVIIa degradation.

In an embodiment, the method of the invention further comprises a step e) of chromatographic separation of the eluted TgFVII and/or TgFVIIa on a size exclusion support. This step is preferably dedicated to TgFVII and/or TgFVIIa polishing and formulation.

In an embodiment, the method of the invention further comprises at least one step of eliminating and/or inactivating viruses, preferably by nanofiltration and/or by Solvent/ Detergent treatment.

In an embodiment, the method of the invention further comprises the final steps of formulating, sterilizing and lyophilizing the purified TgFVII and/or TgFVIIa.

In an embodiment, during the step of affinity chromatography, the method of the invention further comprises the steps of:

(a) loading a chromatographic resin on which a ligand as defined above is immobilized, with milk from a transgenic female rabbit containing recombinantly produced TgFVII and/or TgFVIIa, under conditions allowing the ligand to bind TgFVII and/or TgFVIIa;

(b1) washing the unbound material;

(b2) washing contaminants having an affinity with the ligand weaker than TgFVII and/or TgFVIIa; and (b3) eluting TgFVII and/or FVIIa from the resin.

In an embodiment, during the affinity chromatography step of the method of the invention, said second washing step for removing weak bound material is performed with a buffer comprising from 10% to 50% of a hydrophobic agent, and the ionic strength of which is ranging from 200 to 600 mM.

In an embodiment, during the affinity chromatography step of the method of the invention, said elution step for eluting TgFVII and/or TgFVIIa from the resin is performed with a buffer comprising from 20% to 70% of a hydrophobic agent, and the ionic strength of which is ranging from 500 to 2500 mM.

Further features and advantages of the invention will appear from the following description of embodiments of the invention, given as non-limiting examples, with reference to the accompanying drawings listed hereunder.

BRIEF DESCRIPTION OF THE DRAWINGS

FIG. 1 displays a schematic representation of IgG1, IgG2 and IgG3 forms of Camelidae immunoglobulins having heavy polypeptide chains and devoid of light chains.

FIG. 2 displays the schematic representation of RMP clearance during the process of the invention. The RMP level is indicated in ppm as a function of the step of the process.

FIG. 3 displays the schematic representation of DNA clearance during the process of the invention. The DNA level is indicated in ppb as a function of the step of the process.

FIG. 4 displays the activation of TgFVII through the purification process. Lanes 1-9 respectively correspond to: lanes 1 and 9: Molecular weight, lane 2: clarified milk, lane 3: FVII-selected eluate (after affinity chromatography on the ligand of the invention), lane 4: intermediate product 1 (after ultrafiltration and diafiltration), lane 5: nanofiltrate, lane 6: QSXL eluate, lane 7: CHT-I eluate, lane 8: SEC pool.

FIG. 5 displays a histogram of the viral load in samples after the step of prefiltration and of solvent/detergent treatment (sample named Initial Load) and after elution on affinity FVII Select chromatography (sample named Eluate A).

DETAILED DESCRIPTION OF THE INVENTION

Transgenic Factor VII or Factor VIIa

The purification method of the invention in particular relies on the use of a ligand showing a specific affinity for transgenic Factor VII (TgFVII) and/or transgenic activated Factor VII (TgFVIIa).

The amino acid sequences of transgenic Factor VII and Factor Vila for use in the present invention are known. The amino acid sequence of transgenic Factor VII is in particular identical to the amino acid sequence of human Factor VII, such as disclosed in U.S. Pat. No. 4,784,950.

Source Biological Material

The method of the invention is especially useful for purifying transgenic FVII and/or FVIIa obtained from various biological sources, which are herein referred to as "source biological material".

In one embodiment of the invention, the source biological material contains transgenic FVII and/or FVIIa and is obtained from fractionation of a body fluid from a transgenic animal that has been modified (or is the progeny of an animal that has been modified) to produce transgenic FVII and/or FVIIa. The transgenic animal is preferably a mammal, e.g. a cow, rabbit, goat, sheep, etc. Preferably the source biological material containing TgFVII and/or TgFVIIa is a sample of mammalian milk, i.e. a sample of transgenic mammalian milk producing transgenic FVII and/or FVIIa in its milk.

Methods for producing the transgenic FVII protein in the milk of a transgenic animal may include the following steps: a synthetic DNA molecule containing a gene that codes the transgenic FVII (the amino acid sequence of which corresponds to that of human FVII), which gene is controlled by a promoter of a protein that is naturally secreted in milk, is transferred into an embryo of a non-human mammal. The embryo is then introduced into a female mammal of the same species, which then gives birth to a transgenic animal. Once the subject is sufficiently developed, lactation of the mammal is induced and the milk is collected. The milk then contains the desired recombinant protein. One example of a process for the preparation of the transgenic FVII (TgFVII) in the milk of a female mammal other than a human being is provided in EP 0 527 063. In such specific embodiment, a plasmid containing a WAP promoter is constructed through the introduction of a sequence containing the promoter for the WAP gene, and this plasmid is created in such a way that it can receive a foreign gene that is rendered dependent upon the WAP promoter. The gene that codes for the transgenic FVII is incorporated and rendered dependent upon the WAP promoter. The plasmid containing the promoter and the gene that codes the transgenic FVII protein is used to obtain transgenic animals, such as rabbits, via microinjection into the male pronucleus of rabbit embryos. The embryos are then transferred to the oviduct of hormonally prepared females.

Purification Methods

The invention provides methods for purifying transgenic FVII and/or FVIIa. Such methods in particular involve contacting a source biological material containing TgFVII and/or TgFVIIa with a ligand which is highly specific to TgFVII and TgFVIIa.

The production of transgenic FVII or FVIIa (TgFVIIa) into the milk of transgenic rabbits results in the presence of numerous impurities that have to be eliminated. The process of the present invention is especially designed for purifying the transgenic FVII or FVIIa (TgFVIIa) from the milk of transgenic rabbits, while removing the accompanying contaminating molecules so called Host Related Impurities (HRI), that include Rabbit Milk Proteins (RMP) but also rabbit DNA and other molecules that could contaminate rabbit milk as rabbit serum proteins. Residual serum proteins (e.g. albumin, rabbit FVII, immunoglobulins and transferrin) may be introduced into the milk source material due to passive leakage from the blood stream into the milk.

Milk indeed corresponds to a non-sterile colloidal suspension of soluble whey proteins, insoluble casein micelles and milk fat globules. TgFVII, which is synthesized and secreted by the mammary epithelial cells, is found in the soluble whey fraction. Potential contaminating RMP include, but are not limited to: caseins; lactalbumin, lactoglobulin and lactoferrin. Five families of proteins: transferrin, caseins, albumin, whey acid protein and immunoglobulin (Ig)—were shown to represent approximately 90% of total rabbit milk proteins.

Further, in an embodiment of the present invention, the purification process of the invention is also designed to activate the zymogen TgFVII expressed in the milk, into TgFVIIa. Unfortunately, once activated, TgFVIIa becomes sensitive to supplementary cleavage. TgFVII and/or TgFVIIa cleavage will lead to TgFVII partially or totally missing Gla rich regions or lead to Light (LC) or Heavy Chain (HC) cleavage that could limit the potency of the molecule. In process degradation of TgFVIIa into non active cleaved products or in process TgFVII oxidation are therefore possible and have to be eliminated for guarantying the therapeutic suitability of FVII.

Clarification

Milk clarification as early treatment of milk could be optionally performed by procedures as described in the patent applications WO2007/138198 or WO2008/099077, but there is no limitation of milk treatment before applying the present invention. Optionally clarification could also be bypassed, for example if the first step of the process is performed by a fluidized bed affinity capture. Optionally a fat decantation or skim separation by any technology available in the milk industry could also be performed before purification. In an embodiment of the invention, preferably, milk is mixed with a citrate buffer to obtain quickly a stabilized plasma-like phase of milk then fat separation is obtain by liquid phase separation such as centrifugation or decantation followed by depth filtration. In an embodiment of the invention, preferably depth filtration is performed advantageously for preparing full biologic active molecules of TgFVII and/or TgFVIIa by combination of low shear stress, non-oxidative technology, and quick Bioburden decreasing and size retention of related impurities coming from the milk collection. In such an embodiment, depth filter relative pore size ranges from 30 to 0.1 µm and the depth filtration is preferably implemented by a sequential 25 to 0.5 µm filtration followed by 0.5 µm to 0.1 µm filtration. Cellulose based depth filters are well adapted to this step with or without granular adjuvant or other filter aid compounds. In an embodiment of the invention, the citrate salt concentration and the process temperature range from 0.15 M to saturated citrate salt and from 15° C. to 30° C., and preferably from 0.2 M to 0.5 M citrate salt and from 22° C. to 27° C. These combinations of citrate salts and temperature are necessary to maintain the size populations of milk proteins under the micron order and to obtain a clear plasma-like phase solution. By "clear", it is meant that the clarified milk in the process of the invention displays a controlled turbidity of under 500 NTU (normalized turbidity unit) or an optical density read on spectrophotometer at λ400 nanometer under 1000 AU (relative absorbance unit).

In these conditions, membrane filtration with 0.2 µm pore size can be advantageously performed to reduce the Bioburden charge in the biological source of proteins.

The resulting Bioburden-reduced and stabilized solution could optionally be stored at low temperature under −20° C. for several months.

Affinity Chromatography on a Specific Ligand

The Ligand

The method of the invention for purifying TgFVII/TgFVIIa from a source biological material comprises at least one step of separation by affinity chromatography on a ligand which is specific for transgenic FVII/FVIIa.

In an embodiment of the invention, said affinity ligand, is an isolated antigen-binding protein comprising two heavy polypeptide chains forming a complete antigen binding site or several antigen binding sites, which is further devoid of light polypeptide chains. The antigen-binding protein used in the method of the invention is thus typically composed of a dimer of heavy chains and is devoid of light chains. The two heavy polypeptide chains are sufficient for forming one or more complete antigen binding sites. By "a complete antigen binding site", it is meant according to the invention a site which will alone allow the recognition and complete binding of an antigen, which can be verified by any known method regarding the testing of the binding affinity.

The heavy chains of the antigen-binding protein used in the method of the invention do not have special features for interacting with corresponding light chains (which are absent), and are thus very different from common heavy chains of immunoglobulins. Despite their particular structure, the said antigen-binding proteins are nevertheless capable of showing functional properties which are at least equivalent and preferably improved when compared to standard four-chain model immunoglobulins. The heavy chains forming the said antigen-binding protein thus appear to be intrinsically more suitable for secretion by prokaryotic and lower eukaryotic cells.

In a particular embodiment, the antigen-binding proteins used as affinity ligands in the method of the invention are characterized in that their heavy polypeptide chains contain a variable region (VH) and a constant region (CH), but are devoid of the first domain of their constant region, called CH1. These antigen-binding proteins having no CH1 domain are thus such that the variable region of their chains is directly linked to the hinge region at the C-terminal part of the variable region. WO 94/25591 discloses methods for the preparation of such heavy chains antibodies, or fragments thereof, on a large scale comprising transforming a mould or yeast with an expressible DNA sequence encoding said antibody or fragment. In an embodiment of the invention, the said antigen-binding protein may also be obtained as described in WO 94/04678.

The variable domain of a heavy-chain immunoglobulin as used in the method of the invention has no normal interaction sites with the VL or with the CH1 domain, which do not exist in the heavy chain immunoglobulins. Such immunoglobulins are also commonly designated "VHH" in the literature.

In an embodiment, the antigen-binding proteins used as ligands in the method of the invention are characterized in that their variable regions contain in position 45, an amino acid which is different from leucine, proline or glutamine residues.

In a particular embodiment, the antigen-binding proteins used as affinity ligands in the method of the invention are characterized in that their variable region comprises frameworks (FW) and complementarity determining regions (CDR), especially 4 frameworks and 3 complementarity regions. They thus distinguish from the standard four-chains immunoglobulins especially by the fact that this variable region can itself contain an antigen binding site or several, and does not require the contribution of the variable region of a light chain.

The amino-acid sequences of frameworks 1 and 4 comprise among others respectively amino-acid sequences which can be selected from the following:

for the framework 1 domain:

```
                             (SEQ ID NO: 1)
GGSVQTGGSLRLSCEISGLTFD (SEQ ID NO: 2)
GGSVQTGGSLRLSCAVSGFSFS (SEQ ID NO: 3)
GGSEQGGGSLRLSCAISGYTYG (SEQ ID NO: 4)
GGSVQPGGSLTLSCTVSGATYS (SEQ ID NO: 5)
GGSVQAGGSLRLSCTGSGFPYS (SEQ ID NO: 6)
GGSVQAGGSLRLSCVAGFGTS (SEQ ID NO: 7)
GGSVQAGGSLRLSCVSFSPSS;
``` for the framework 4 domain:

```
                             (SEQ ID NO: 8)
WGQGTQVTVSS (SEQ ID NO: 9)
WGQGTLVTVSS (SEQ ID NO: 10)
WGQGAQVTVSS (SEQ ID NO: 11)
WGQGTQVTASS (SEQ ID NO: 12)
RGQGTQVTVSL,
``` and/or,
for the CDR3 domain

```
                             (SEQ ID NO: 13)
ALQPGGYCGYGX---------CL (SEQ ID NO: 14)
VSLMDRISQH-----------GC (SEQ ID NO: 15)
VPAHLGPGAILDLKKY------KY (SEQ ID NO: 16)
FCYSTAGDGGSGE---------MY (SEQ ID NO: 17)
ELSGGSCELPLLF---------DY (SEQ ID NO: 18)
DWKYWTCGAQTGGYF-------GQ (SEQ ID NO: 19)
RLTEMGACDARWATLATRTFAYNY (SEQ ID NO: 20)
QKKDRTRWAEPREW--------NN (SEQ ID NO: 21)
GSRFSSPVGSTSRLES-SDY-NY (SEQ ID NO: 22)
ADPSIYYSILXIEY--------KY (SEQ ID NO: 23)
DSPCYMPTMPAPPIRDSFGW-DD (SEQ ID NO: 24)
TSSFYWYCTTAPY---------NV (SEQ ID NO: 25)
TEIEWYGCNLRTTF--------TR (SEQ ID NO: 26)
NQLAGGWYLDPNYWLSVGAY-AI (SEQ ID NO: 27)
RLTEMGACDARWATLATRTFAYNY (SEQ ID NO: 28)
DGWTRKEGGIGLPWSVQCEDGYNY (SEQ ID NO: 29)
DSYPCHLL--------------DV (SEQ ID NO: 30)
VEYPIADMCS------------RY
```

In an embodiment, the constant region of the antigen-binding protein comprises CH2 and CH3 domains comprising an amino-acid sequence selected from the following group of sequences:

for the CH2 domain:

```
                             (SEQ ID NO: 31)
APELLGGPTVFIFPPKPKDVLSITLTP (SEQ ID NO: 32)
APELPGGPSVFVFPTKPKDVLSISGRP (SEQ ID NO: 33)
APELPGGPSVFVFPPKPKDVLSISGRP (SEQ ID NO: 34)
APELLGGPSVFIFPPKPKDVLSISGRP
``` for the CH3 domain:

```
                             (SEQ ID NO: 35)
GQTREPQVYTLA
```

GQTREPQVYTLAPXRLEL (SEQ ID NO: 36)

GQPREPQVYTLPPSRDEL (SEQ ID NO: 37)

GQPREPQVYTLPPSREEM (SEQ ID NO: 38)

GQPREPQVYTLPPSQEEM (SEQ ID NO: 39)

Preferably, the antigen-binding proteins are characterized in that their hinge region comprises from 0 to 50 aminoacids. Particular regions of hinge regions of these proteins are the following sequences:

GTNEVCKCPKCP, (SEQ ID NO: 40)

or

EPKIPQPQPKPQPQPQPQPKPQPKPEPECTCPKCP (SEQ ID NO: 41)

The short hinge region corresponds to an IgG3 molecule and the long hinge sequence corresponds to an IgG2 molecule.

In a particular embodiment, the antigen-binding proteins used as ligand in the method of the invention can be isolated from animals, more specifically from Camelidae, and preferably from the blood of Camelidae. In a further embodiment, the antigen-binding proteins are derived from Camelidae immunoglobulins, and more specifically from immunoglobulins from Old world camelids (*Camelus bactrianus* and *Camelus dromedarius*) or new world camelids (*Lama pacos, Lama glama* and *Lama vicugna*). Depending on the animal they are originating from, the molecular weight of the antigen-binding proteins can be from approximately 43 kDa to approximately 47 kDa, in particular 45 kDa.

In an embodiment, these antigen-binding proteins may have been modified and especially humanized, through the replacement of all or part of their constant region by all or part of a constant region of a human antibody. For example, the CH2 and/or CH3 domains of the said antigen-binding proteins could be replaced by the CH2 and/or CH3 domains of the IgG γ3 human immunoglobulin. In such humanized antigen-binding proteins, a part of the variable sequences, and in particular one or more of the framework residues which do not intervene in the binding site, may also have been replaced by human antibody framework residues. Said antigen-binding proteins can comprise type G immunoglobulins and especially immunoglobulins which are defined as immunoglobulins of class 2 (IgG2) or immunoglobulins of class 3 (IgG3).

The advantages of the above described antigen-binding protein rely on the fact that the lack of a light chain variable domain means that the extra dimension of variability in the antibody repertoire resulting from the possibility of pairing different combinations of variable domains is not present, so that it is possible to prepare antigen-binding proteins directed to a specific antigen (here transgenic FVII/FVIIa) in avoiding the generation of large numbers of irrelevant antigen-binding proteins. A second advantage is that VHH domains have been shown to be significantly more stable than traditional antibodies, so that chromatographic separations based on said antigen-binding proteins are expected to be significantly more robust. Further, the lack of dependence on interaction with a light chain variable domain for maintaining structural and functional integrity gives these VHH domains a substantial advantage over other small antibody fragments, in terms of ease of production and behavior in solution. In particular, VHH fragments are molecules especially suited for immuno-affinity purification, because of their unusual stability and their ability to refold efficiently after complete denaturation, which frequently occurs during elution of the antigen.

When the affinity ligand used in the method of the invention is an antigen-binding protein as defined above, it can be directed against any epitope of transgenic FVII/FVIIa, provided that said epitope is specific to transgenic FVII/FVIIa. Such epitopes comprise any structure composed of aminoacids, polypeptides, carbohydrates, or mixture thereof.

By the expression "ligand which is specific for transgenic FVII/FVIIa", it is meant that the ligand used for the affinity chromatography step of the invention does not substantially bind to, or restricts substantially the binding of any other protein, including FVII or FVIIa from other species, such as rabbit or goat FVII or FVIIa. The ligand used in the invention preferably possesses an affinity of more than 1 µM toward transgenic Factor VII or Factor VIIa, and may advantageously have an affinity of at least 100 nM and more preferably of from 1 to 10 nM for transgenic FVII or FVIIa. In a particular embodiment, the ligand used in the invention binds transgenic FVII or FVIIa with more than one log difference when compared to rabbit FVII or FVIIa. By the expression "restricts substantially the binding of proteins", it is meant that the ligand used in the invention permits at least 4 logs or 99.99% removal of Host Related Impurities (HRI) contained in the initial solution loaded onto the chromatographic support, and at least 3 logs or 99.9% removal of FVII or FVIIa proteins endogenously produced by the transgenic mammal used for expressing transgenic FVII.

In an embodiment, the mass of endogenous Factor VII or Factor VIIa in the fraction eluted from the affinity support is reduced 100-fold, preferably 1000-fold, or most preferably 10000-fold or more with respect to the mass of these proteins within the initial solution loaded onto the column. In comparison the relative mass of transgenic Factor VII or Factor VIIa loaded on the FVII-specific ligand and recovered in the elution fraction is at least 30%, preferably at least 50% or more of the mass of these proteins within the initially loaded solution.

In a particular embodiment, the antigen-binding protein of the invention (ligand) has the following kinetic binding constants: $Ka=2.58\times10^8$ M and $Kd=9.88\times10^{-8}$M.

Any functional fragment or functional derivative of the above described antigen-binding proteins may also be used as ligand for binding specifically transgenic Factor VII and/or activated transgenic Factor VII (FVIIa) in the method of the invention.

A "functional fragment" of the above described antigen-binding proteins is a fragment that shows a strong affinity for human Factor VII or Factor VIIa, and preferably substantially the same affinity with respect of human FVII or FVIIa than the antigen-binding protein from which it originates, or at least about 50%, still preferably at least about 60, 70, 80, or 90% of the affinity shown by the antigen-binding protein from which it originates.

Fragments encompassed for use as ligand in the method of the invention comprise one heavy polypeptide chain of an antigen-binding protein devoid of light chains, fragments obtained by enzymatic digestion of the above described antigen-binding proteins, especially those obtained by partial digestion with papaïn leading to the Fc fragment (constant fragment) and leading to FVHh fragment (containing the antigen binding sites of the heavy chains) or its dimer F(VHh)2, or a fragment obtained by further digestion with papaïn of the Fc fragment, leading to the pFc fragment corresponding to the C-terminal part of the Fc fragment, homologous fragments obtained with other proteolytic enzymes, fragments of at least 10 preferably 20 amino acids of the variable region of the antigen-binding protein, or the complete variable region, especially a fragment corresponding to the isolated VH domains or to the VH dimers linked to the hinge, and fragments corresponding to at least 10, preferably 20 amino acids of the constant region or to the complete constant region of the antigen-binding protein.

By "functional derivative" it is meant a polypeptide that differs from the antigen-binding protein used as ligand in the method of the invention by one or several substitutions, deletions or additions of amino acids, to the extent the derivative shows binding affinity and specificity with respect to transgenic FVII or FVIIa. The "functional derivative" preferably substantially displays the same affinity than the above described antigen-binding proteins or at least about 90%, still preferably at least about 50, 60, 70, or 80% of the affinity shown by said antigen-binding protein with respect of transgenic FVIIa. Said functional derivative includes homologs that show a high percentage of identity with the above described antigen-binding proteins, to which they are at least 80%, 85% 90%, 95% or 99% identical, and preferably differ from the above described antigen-binding proteins by one or several conservative substitutions.

In an embodiment of the invention, the antigen-binding protein is immobilized on a solid phase. Immobilization may be achieved by adsorption or by chemical cross-linking.

Commonly, attachment of proteins to solid surfaces, such as chromatography media, has been brought about by exposing the surface of a solid phase to a solution of the protein such that the protein is adsorbed onto the solid surface via non-specific binding mechanisms. Methods for immobilizing proteins on chromatography media are well established in the literature, see for example, in Boschetti E., Egly J. M., Monsigny M., 1983, Practical Guide for use in Affinity chromatography and related techniques, $2^{nd}$ edition, IBF Villeneuve-la-garenne, France, pages 1-157. Where the solid surface is provided by a hydrophobic material such as polystyrene, for example, then attachment is generally brought about by adsorption of hydrophobic regions of the protein onto the hydrophobic surface.

Alternatives to, or improvements upon, the method of adsorption of proteins in the preparation of immobilized protein surfaces are available.

One alternative approach is to use chemical cross-linking of residues in the protein for covalent attachment to an activated solid surface using conventional coupling chemistries, for example as described in Boschetti E., Egly J. M., Monsigny M., 1983, Practical Guide for use in Affinity chromatography and related techniques, $2^{nd}$ edition, IBF Villeneuve-la-garenne, France, pages 1-157. Amino acid residues incorporating sulphydryl groups, such as cysteine, may be covalently attached using a bispecific reagent such as succinimidyl-maleimidophenylbutyrate (SMPB), for example.

Alternatively, lysine groups located at the ligand surface may be coupled to activated carboxyl groups at the solid surface by conventional carbodiimide coupling using 1, ethyl-3-[3-dimethyl aminopropyl]carbodiimide (EDC) and N-hydroxysuccinimide (NHS). One can also attach the ligand by using an extension in the form of a peptide tail, immobilized to the solid phase by non-covalent adsorption or using conventional chemical cross-linking agents.

According to one embodiment of the invention, the antigen-binding protein of the invention is attached to a solid phase by covalent cross-linking using conventional coupling chemistries. The solid phase may naturally comprise cross-linkable residues suitable for covalent attachment or it may be coated or derivatized to introduce suitable cross-linkable groups according to methods well known in the art.

The solid phase onto which immobilization takes place may be provided by a variety of materials and may suitably be any solid phase carrier material conventionally used in immobilizing proteins. The method of the invention is applicable with any solid phase material that is amenable to the immobilization of proteins or protein fragments, either directly or after pre-treatment. The carrier materials may be particulate (e.g. beads or granules, generally used in extraction columns) or in sheet form (e.g. membranes or filters, glass or plastic slides, microtitre assay plates, dipstick, capillary fill devices or such like) which can be flat, pleated, or hollow fibres or tubes. The following matrices are given as examples and are not exhaustive, such examples could include silica (porous amorphous silica), e.g. the FLASH series of cartridges containing 60 A irregular silica (32-63 µm or 35-70 µm) supplied by Biotage (a division of Dyax Corp.), agarose or polyacrylamide supports, for example the Sepharose range of products supplied by Amersham Pharmacia Biotech, or the Affi-Gel supports supplied by Bio-Rad. In addition there are macroporous polymers, such as the pressure-stable Affi-Prep supports as supplied by Bio-Rad. Other supports that could be utilised include; dextran, collagen, polystyrene, methacrylate, calcium alginate, controlled pore glass, aluminium, titanium and porous ceramics. In a preferred embodiment, resins are used as the solid phase, including commercial resins such as Sephadex®, Sepharose®, Fractogel®, CIMGEL® Toyopearl®, HEMA®, as well as crosslinked agarose, and macroporous polystyrene or polyacrylate. The solid phase may also be of a mainly inorganic nature, such as macroporous glass or clay minerals, or combinations of resins and inorganics, such as Ceramic HyperD® or silica gel.

Loading Step

The source biological material containing transgenic FVII/FVIIa is optionally pre-treated (e.g. by clarification or filtration steps) before loading on the affinity support comprising the above described ligand.

The source biological material is preferably adjusted before loading on the affinity support comprising the ligand. In an embodiment of the invention, the pH of the loading buffer is adjusted from about 6.0 to 8.0. For the purpose of this chromatographic step of the invention, a suitable loading buffer typically corresponds to an aqueous solution comprising a buffering agent, typically phosphate, citrate, or tris. Nevertheless, all carboxylic or zwitterionic buffers with a pK close to neutrality could also be used. Divalent ions such as calcium, magnesium, zinc, etc could be added to the loading buffer in the range of from 0 to 50 mM (final concentration).

The loading step is typically conducted at a flow rate of 10 to 72 column volumes (CV) per hour, and preferably at 18 to 54 CV/hour. In some embodiments, the loading flow rate ranges from 30 to 48 CV/hour, and preferably from 36 CV/hour. These specific ranges allow a sufficient contact time for the transgenic FVII/FVIIa to the ligand without excessive time to form a non dissociable complex.

In an embodiment of the invention, the loaded material is rinsed after loading on the column, until the non-specific binders and contaminants have eluted.

First Washing Step—Removal of Unbound Material

In an embodiment of the invention, a first washing step is conducted such as to elute the unbound material contained in the loaded solution. Said first washing is preferably performed with a washing buffer having a pH in the range of from 2 to 9. In some embodiments, the pH of the first washing buffer ranges from 3 to 10, from 3 to 7, from 5 to 9, from 6.5 to 8.5 or from 6.5 to 10.0, upon application to the affinity resin. In some interesting embodiments, the pH of the first washing buffer ranges from 4.0 to 7.0, from 7.0 to 9.0, or from 4.5 to 8.5.

During the first washing step, weak interactions between contaminant proteins present in the source material and immobilized ligands can be reduced by such buffer in these specific ranges of pH. Electrostatic repulsion interactions are indeed advantageously used for eluting weakly bound proteins.

The first washing step is typically conducted at a flow rate of 10 to 72 column volumes (CV) per hour, and preferably at 18 to 54 CV/hour. In some embodiments, the washing flowrate ranges from 30 to 48 CV/hour, and is preferably of 36 CV/hour. In an embodiment of the invention, the first washing buffer is an aqueous solution comprising a buffering agent, typically phosphate, or tris. Nevertheless, all carboxylic or zwitterionic buffers with a pK close to neutrality could also be used.

In an embodiment, the first washing buffer comprises 0 to 100 mM, preferably 50 mM Tris Buffer, at a pH between 6.5 and 8.5, and most preferably at pH 7.5.

It should be understood that the washing step may be extended by using one, two or several different washing buffers, or by the application of a gradient washing buffer.

Second Washing Step—Removal of Weak Bound Material

In an embodiment of the invention, a second washing buffer is advantageously applied before elution of TgFVII/TgFVIIa, for eliminating contaminants bound on the resin but having an affinity weaker than TgFVII or TgFVIIa. In an embodiment, the second washing buffer contains an Ether diol compound and at least one soluble salt.

In an embodiment of the invention, the ions concentration of the second washing buffer is increased with sodium chloride or chaotropic salts, as magnesium. In an embodiment, the ionic strength is increased with ionic components such as monovalent or multivalent anionic and/or cationic salt. In an embodiment, the ionic strength or ion concentration ranges 200 to 600 mM, or more preferably from 300 to 500 or 350 to 450 mM. In the same time, the hydrophobicity of the buffer is increased with hydrophobic agents such as ethylene glycol or propylene glycol. In an embodiment, the percentage of hydrophobic agent in the second washing buffer ranges from 10% to 50%, from 20% to 40%, and preferably from 25% to 35%.

By "weak bound material", it is meant that the second washing step triggers the removal of material having an affinity (Kd) of at least 100 µM, preferably of at least 10 µM for the affinity ligand used in the method of the invention.

In an embodiment, the ionic and hydrophobic strengths of the second washing buffer are increased together for removing as much contaminants bound on the affinity resin as possible, and preferably all.

The second washing buffer preferably comprises 0 to 40% of glycol ether and from 0 to 0.5 M of a sodium salt, in tris Buffer at a pH from 6.5 to 8.5. In a preferred embodiment, the second washing buffer comprises 30% Propylene Glycol and 0.4 M NaCl, in Tris Buffer at pH 7.5.

It should also be noted that the second washing step and the elution step need not to be discrete steps, but may be combined, in particular if a gradient elution buffer is used in the elution step.

Elution Step

After the washing step(s), the TgFVII/TgFVIIa bound on the ligand of the affinity column is eluted with an elution buffer, and a purified solution of the TgFVII and/or TgFVIIa is collected as an eluate. Desorption of human FVII or FVIIa is preferably achieved by changing the physicochemical conditions such that the antigen-binding ligand no longer binds human FVII or FVIIa. Elution may be achieved by changing the conditions with respect to pH, salt, temperature or any other suitable measure.

By the expression “disrupting in a non destructive way the interaction with said ligand”, it is meant that the integrity and functionality of the TgFVII and/or TgFVIIa are preserved at the time of eluting said transgenic FVII forms.

In an embodiment, the elution is performed with a buffer having a pH below 3.0, but a quick neutralization to pH over 6.0 is necessary to maintain the biological activity of the eluted molecule.

The elution buffer is typically an aqueous solution comprising a buffering agent, typically phosphate, or tris. Nevertheless, all carboxylic or zwitterionic buffers with a pK close to neutrality could also be used. The elution step is preferably conducted with an elution buffer having a pH from 2 to 10. In some embodiments, the pH ranges from 3 to 9, from 5 to 8 and most preferably from 7 to 8. Electrostatic repulsion interactions are not sufficient to disrupt the specific affinity interactions between TgFVII or TgFVIIa and ligand. The elution buffer may further advantageously comprise any additional component allowing maintaining the TgFVII/TgFVIIa biologically active without loss of post-traductional transformations like glycosylation for example or avoiding its aggregation or oxidation.

Preferably, the ionic strength of the elution buffer is increased with sodium chloride or chaotropic salts as magnesium. In an embodiment, the ionic strength of the elution buffer ranges from 500 to 2500 mM, from 1000 to 1800 mM, or preferably from 1200 to 1600 mM.

Preferably, the hydrophobicity of the elution buffer is increased with hydrophobic agents as ethylene glycol or propylene glycol. In an embodiment, the percentage of the hydrophobic agent in the elution buffer ranges from 20% to 70%, from 30% to 50%, or preferably from 40% to 50%.

Most preferably the ionic strength and hydrophobicity of the elution buffer are increased together in a buffer with a pH from 7 to 8. In an embodiment, the percentage of the hydrophobic agent in the elution buffer ranges from 20% to 60% and its ionic strength ranges from 0.5 to 2.0 M. Preferably, the percentage of the hydrophobic agent ranges from 30% to 50% and the ionic strength ranges from 1.0 to 1.8 M, or the percentage of the hydrophobic agent ranges from 40% to 50% and the ionic strength ranges from 1.2 to 1.6 M.

In a preferred embodiment, the desorption of active and stable TgFVII and/or TgFVIIa molecules is performed with a buffer that comprises 45% Propylene Glycol and 1.5M Sodium Chloride in tris Buffer pH 7.5.

The elution step is typically conducted at a flow rate of 10 to 72 column volumes (CV) per hour, and preferably at 18 to 54 CV/hour. In some embodiments, the elution flowrate ranges from 30 to 48 CV/hour, and is preferably of 36 CV/hour. When the flow rate is increased, the potential re-association to free immobilized ligand is reduced and TgFVII recovery in the eluate fraction is improved. This effect is mainly related to the strong affinity of the ligand for the TgFVII or TgFVIIa.

After affinity purification as proposed in the invention, more than 90% pure TgFVII/TgFVIIa is prepared, representing more than 4 decimal logarithmic rabbit milk proteins (RMP) reduction (4 $\log_{10}$ or 99.99% reduction). Nevertheless, RMP are typically below 500 000 ppm, preferably below 100 000 ppm and most preferably below 50 000 ppm. Rabbit transferrin has been shown to be one of the most important accompanying contaminating RMP.

In order to reduce RMP to a very low level, typically below 5 ppm, the purification scheme has to integrate various orthogonal methods. By "orthogonal methods", it is meant multistep purification procedures employing separation mechanisms that are distinct from one another. In the present invention purification is based on chromatographic methods because of their selectivity, efficiency and simplicity to scale up. The combination of those methods was specifically designed to ensure a final high TgFVII and/or TgFVIIa quality, free of aggregates and with very low levels of degraded and oxidized forms.

Moreover, Applicant has discovered unexpected and surprising properties of the affinity chromatography, specifically its capacity to improve the reduction of viral titer for enveloped virus such as Murine Leukaemia Virus (MLV) and for non-enveloped virus such as Porcine ParvoVirus (PPV).

In a particular preferred manner, the step of affinity chromatography is performed to obtain a viral reduction factor (RF) superior to 3 $\log_{10}$, preferably superior to 4 $\log_{10}$, more preferably superior to 5 $\log_{10}$.

By "viral reduction factor", it is meant the resultant of the ratio between the value of viral quantity (titer×volume) measured before the implementation of chromatographic step (I.e. the value of viral titer of initial load) and the value of viral quantity (titer×volume) measured after the implementation of chromatographic step (i.e. the value titer measured in the eluate). The viral titer is calculated using the Spearman Karber equation as described in the Federal Gazette No 84, May 4, 1994, and in Schmidt, N.J. & Emmons, R. W. (1989) in Diagnostic Procedures for Viral, Rickettsial and Chlamydial Infection, 6th Edition.

Ultrafiltration/Diafiltration

According to the present invention, the affinity purified material could be diafiltered or diluted to reduce the ionic strength prior to be further purified. In an embodiment of the invention, ultrafiltration membrane with a cut-off range from 5 to 50 kDa, preferably 10 to 30 kDa is used. By buffer exchange, the ionic strength is decreased to a range of 1 to 50 mM and preferably 5 to 15 mM of buffer containing a sodium salt and, in an embodiment of the invention a trisodium citrate salt.

In an embodiment of the invention, long term storage could be advantageous done at this step and preferably at low temperature, under −20° C.

In an embodiment of the invention, the affinity purified material stabilized by salt reduction, by long term storage and by microorganisms removal could be further purified.

Ion Exchange Chromatography

According to a preferred embodiment of the invention, the process of the invention further comprises at least one ion exchange chromatography step in order to further purify TgFVII and TgFVIIa.

Preferably, at least one chromatography step is performed on anion exchange resin. Said anion exchange chromatography could be implemented with a strong or weak base type chromatographic support. In some embodiment, quaternary ammonium functionalized group from different commercial resins are usable like Q-Sepharose from GE Healthcare, and most preferably like the Q Sepharose XL type. The list is not limitative and strong anionic exchangers from Bio-Rad, Pall Biosepra, Merck, Millipore ore other suppliers could be used.

Advantageously, TgFVII activation into TgFVIIa increases during the separation step performed on the anion exchanger.

Loading Step

The prepurified material is adsorbed to the anionic support firstly equilibrated in the same range of conductivity and the same salt as a use.

In an embodiment of the invention a salt change is introduced just after loading to reinforce the RMP interaction to the anionic charge. The sodium salt and more particularly trisodium citrate salt is switched to an imidazole buffer with a lower conductivity. In this specific buffer, imidazole ranges from 1 to 50 mM and preferably from 5 to 30 mM and more preferably 20 mM. The pH of the buffer is also maintained in the range of 6.5 to 8.5 and preferably 7 to 8. In such conditions, Transferrin and non-active TgFVII or TgFVII complexed to other proteins show an interaction reinforced to the anion exchange resin.

First Wash

In an embodiment of the invention, a first wash is applied by increasing salt concentration and especially sodium chloride salt concentration in a range between 50 and 175 mM and more preferably between 130 and 160 mM. This wash could be applied by gradient or by step. In an embodiment of the invention, this wash shows a specific elution of milk endogenous transferrin, while, in the same time, in the presence of imidazole buffer, TgFVII/TgFVIIa stay onto the ionic gel and traces of transgenic FVII complexed to other proteins is also maintained adsorbed.

TgFVII/TgFVIIa Elution

In the embodiment of the invention, TgFVII/TgFVIIa is eluted from the anionic exchanger by decreasing the salt concentration and especially the sodium chloride salt concentration in a range between 0 to 75 mM and more preferably between 40 to 60 mM and in the same time, by introducing a calcium salt at very low concentration, in the range of 2 to 9 mM and more preferably between 5 and 8 mM. Specific interaction of calcium with gla-domain containing proteins such as FVII molecule has been studied for a long time. Conformational change in the FVII molecule leads to a global charge change allowing elution at low conductivity. In an embodiment of the invention, in presence of imidazole, traces of TgFVII complexed to other proteins are maintained adsorbed. Other salts like tris-hydroxymethyl aminomethane or trisodium citrate show a co-elution of free TgFVII and/or with TgFVII complexed to other proteins TgFVII eluted from the anionic exchanger comprises from 50% to 100% activated forms of TgFVIIa and more preferably from 80 to 100%.

Moreover, Applicant has discovered unexpected and surprising properties of the ion exchange chromatography, specifically its capacity to improve the reduction of viral titer for enveloped virus such as Murine Leukaemia Virus (MLV) and for non-enveloped virus such as Porcine Parvo-Virus (PPV).

In a particular preferred manner, the step of ion exchange chromatography is performed to obtain a viral reduction factor (RF) superior to 3 $\log_{10}$, preferably superior to 4 $\log_{10}$, more preferably superior to 5 $\log_{10}$.

Pseudo-Affinity Chromatography, Preferably on Hydroxyapatite In an embodiment of the invention, the eluate collected from the anion exchange chromatography and containing TgFVII and/or TgFVIIa is further purified by pseudo-affinity chromatography advantageously on a hydroxyapatite gel ($Ca_{10}(PO_4)_6(OH)_2$).

This additional pseudo-affinity chromatography is preferably performed under the following conditions: the column is equilibrated with an aqueous buffer A comprising from 10 to 30 mM potassium or sodium phosphate or of a mixture thereof, at a pH between 7.5 to 8.5.

The TgFVII/TgFVIIa molecules formulated with calcium are retained on the support, while Des-gla-FVII and other cleavages are removed in the flowthrough (by "Des-Gla-FVII", it is meant a FVII the GLA domain of which has been removed, possibly by proteolysis).

The percolation of the buffer A, just after the loading step, elute a part of TgFVII and/or TgFVIIa partially cleaved during the process and this allows a good elimination of undesirable FVII forms, such as low active or inactive TgFVIIa.

The elution of TgFVIIa is performed with a buffer comprising a phosphate salt, such as sodium or potassium phosphate, or a mixture thereof, in a predetermined concentration, preferably representing a buffer B comprising from 0.1 M to 0.5 M sodium phosphate and preferably from 0.1 M to 0.2 M with a pH between 7.5 and 8.5. The resulting eluate contains the fully active TgFVIIa, with a low percentage of cleaved forms.

Size Exclusion Chromatography

The final traces of RMP could be only identified by mass spectrometry or by specific ELISA. Before the final polishing step, RMP are ranging between 50 and 500 ppm and are most preferably bellow or equal to 300 ppm.

In an embodiment of the invention, a further purification step may be performed by size exclusion chromatography. Size exclusion column height, resin porosity and chromatography buffer have to be selected in order to reach the best selectivity. High performance resins equivalent to Superdex S75 prep grade or more preferably Superdex S200 prep grad are required for the polishing step. Gel bed height greater than 60 cm and lower than 120 cm and more preferably greater than 80 cm and lower than 110 cm allows enough resolution to remove 2 additional logs of RMP traces.

In an embodiment the buffer exchange applied during the SEC contains a non-ionic detergent at a concentration between 20 to 500 ppm, or preferably from 50 to 200 ppm in combination to amino acids like arginine or glycine or sugar with no limitation. The presence of the ionic detergent in the buffer advantageously help to maintain the monomeric state of the TgFVII/TgFVIIa during SEC, leading to an optimal separation between FVII and contaminating molecules. In an embodiment of the invention, the formulation buffer contain mixtures of different amino acids with sorbitan monolaurate or/and monooleate as described in the US Patent 2012/0087908. A linear flow rate between 10 and 40 cm/hr, more preferably between 20 and 25 cm/hr combined with a loading volume ranging from 1% to 10% of the SEC column volume, more preferably from 2 to 5% of the SEC column volume is applied to obtain a monomeric peak of TgFVII and/or TgFVIIa bellow 5 ppm of RMP or a purity greater than 99.9995%.

Moreover, Applicant has discovered unexpected and surprising properties of the size exclusion chromatography, specifically its capacity to improve the reduction of viral titer for enveloped virus such as Murine Leukaemia Virus (MLV) and for non-enveloped virus such as Porcine Parvo-Virus (PPV).

In a particular preferred manner, the step of size exclusion chromatography is performed to obtain a viral reduction factor (RF) superior to 3 $\log_{10}$, preferably superior to 4 $\log_{10}$, more preferably superior to 5 $\log_{10}$.

Thus, the affinity chromatography step and/or of ion exchange chromatography step and/or of size exclusion chromatography step allow to obtain a viral reduction factor (RF) superior to 3 $\log_{10}$, preferably superior to 4 $\log_{10}$, more preferably superior to 5 $\log_{10}$.

Elimination/Inactivation of Viruses

The method of the invention may also comprise at least one viral inactivation/removal dedicated step but most preferably at least two orthogonal viral inactivation/removal dedicated steps have to be included. The clarified milk could be virally inactivated by chemical treatment with solvent and/or detergent treatment or other types of efficient treatment. In an embodiment of the invention solvent/detergent is used, in particular in the presence of a mixture of Tween® 80 (1% to 1.5% w/v) and of TnBP (tri-n-butyl phosphate 0.3% to 0.5% v/v), to inactivate enveloped viruses. Other non-ionic detergents like Octoxynol100 or Triton X114 or Sodium Cholate or Tween® 20 with no limitation could also replace or complement the Tween® 80.

Moreover, the eluate resulting from any of the described chromatographic steps may be subjected to a step of nanofiltration in order to eliminate efficiently the viruses, in particular the non-enveloped viruses, such as the parvovirus B19. It is in particular possible to use the filters ASAHI PLANOVA™ 15 retaining the viruses with a size greater than 15 nm.

In an embodiment of the invention, nanofiltration is preferably performed after the first chromatographic step, where the TgFVII purity is more than 90% and the main part of high molecular sizes of protein like caseins micelles are enough removed to allow the filtration in such pore size nanofilters. Starting FVII concentration is preferably between 1.0 and 2.5 g/L and more preferably between 1.3 and 2.2 g/L and a typical flow rate is between 5 and 15 LMH, preferably between 8 and 12 LMH (by "LMH", it is meant Liters per square Meter per Hour, or $L/m^2/h$).

In addition to the viral removal, nanofiltration shows also the advantageous reduction of the endogenous DNA by a sieving mechanism through the wideness of nanofilters.

In an embodiment of the invention, nanofiltration filters equivalent to Planova15 nanometer mean pore size could be used. 20 nanometer pore size filter could replace the 15 nanometer filter and the 15 nanometer filter could be coupled to filter with higher porosity. In an embodiment of the invention a sequential 0.2 μm/0.1 μm followed by a Planova 20 nanofilter followed by a Planova 15 nanofilter could advantageously reduce any risk in the same time (bioburden, mycoplasma, viruses, adventitious agents, TSE) without loss of the biological activity of TgFVII/TgFVIIa.

Formulation, Sterilisation, Lyophilisation

Once the last eluate containing the purified TgFVII and TgFVIIa is recovered, said eluate could be submitted to a filtration step on 0.22 μm filters, filled in containers and then freezed/dried.

Preferably, modified PVDF membrane are advantageously used in the invention due to the low binding of proteins and the low adsorption of non-ionic detergent described by the furnishers. Durapore® Membrane filters from Millipore is well adapted to this step with no limitation of others commercial filters.

The below examples illustrate the invention without limiting its scope.

EXAMPLES

Example 1: Preparation of Specific Anti-FVII/FVIIa Ligands

A *lama* was immunized with highly pure human FVIIa antigen. Following the second boost, a more than 100-fold increased titer was observed, indicating a specific enrichment against the human FVIIa/FVII antigens. RNA was collected from the *lama* and VHH expression libraries were generated. Clones were tested in ELISA for expression of *lama* VHHs with the ability to bind to human FVIIa. 23 VHH clones were selected and further tested for their capacity to bind plasma derived human FVII and FVIIa and recombinant rabbit FVII. All clones were found capable to bind to human FVII and FVIIa, and no cross-binding was observed towards recombinant rabbit FVII. The clones were further tested for their binding and elution capacities with respect to FVII/FVIIa, as well as for the stability of their binding properties at acidic pH. A selected candidate was re-cloned into BAC's yeast expression system and corresponding ligands were expressed, then coupled on NHS-Sepharose at a ligand density of 2.5 mg per ml matrix.

Example 2: Purification of TgFVIIa from Milk

The present example describes the preparation of a highly purified activated TgFVII solution from 150 liters of rabbit milk.

2.1 Milk Collection

The composite starting pool of milk consisted in a complete lactation cycle of mini-pools from 6 daily collected milk, filled together in 1 L bottle, sampled for biological safety controls (Bioburden, endotoxins and endogenous virus) then saved and frozen at very low temperature (<−60° C.) for a long time storage (several months at <−20° C.). Milk was collected from Day 4 to Day 24 corresponding to a natural cycle of milking.

2.2 Clarification

Frozen Bottles containing milk were placed in a large thawing tank maintained at 32-37° C. The thawing time was around 1 hour to obtain the last piece of ice in each bottle. 147.4 kg of thawed Source Material (SM) were transferred and pooled in a 500 L mixing system bag. 0.315 M tri-sodium citrate buffer was added to obtain a protein concentration in range 20 to 40 g/L. Temperature of the mixture was adjusted to 24-26° C. The mixing system was stopped to allow fat decanting in the upper layer of the diluted and citrated SM.

Depth Filters with range of pore size between 15 and 0.5 μm (PDH4) and between 0.3 and 0.1 μm (PEKS) handled with a STAX device (Pall Corporation) were preliminary equilibrated in buffer. Milk treated with citrate buffer was filtrated and 444 Kg of filtrate were filled in a single use bag before performing a 0.2 μm filtration with 0.45/0.2 μm Sartobran® Filtrer (Sartorius Corporation). The filterability of the different filters were adapted for filtering without clogging from around 2 to 15 kg of proteins by square meter depending of the progressive mean pore size.

2.3 S/D Treatment

Addition of solutions of Polysorbate 80 and Tri-n-Butyl Phosphate was done to the clarified source of material (CSM) to obtain 509.8 Kg of solution containing 0.8-1.5% w/v Detergent and 0.2-0.5% v/v solvent. Temperature was adjusted to 25±2° C. and at least 2 hours of contact time in such conditions were maintained to inactivate any potential non-enveloped viruses in the biological source. Traces of residual lipids or triglycerides coming from the milk were also chemically dissolved by the addition of detergent and solvent, making a solution more suitable for the further chromatographic steps.

2.4 Affinity Chromatography on Transgenic FVII/FVIIa Specific Ligand

The column was equilibrated with 50 mM tris buffer at pH 7.5, then the solution containing the proteins was loaded at 220 L/H. 6 Liters of affinity gel was large enough to adsorb all TgFVII from the treated milk pool. After loading, the first washing was done with tris buffer. 90 liters were necessary to guarantee a stable baseline return. Proteins bound by nonspecific interactions were removed during this large wash.

An optimized washing step for maximizing RMP elution and minimizing FVII desorption was performed by increasing the ionic strength to 500 mM of sodium chloride and the relative hydrophobicity with 30% v/v propylene glycol to the initial tris buffer.

An optimized elution step for minimizing RMP desorption and maximizing FVII elution was performed by increasing the ionic strength to 1500 mM of sodium chloride and the relative hydrophobicity with 45% v/v propylene glycol.

50.6 liters were collected in the affinity eluate fraction. The amidolytic FVII/antigenic FVII ratio of the affinity eluate was close to 1 corresponding to 1 unit of clotting factor for 1 unit of antigen molecule. The affinity step enabled the removal of the main part of the RMP with a 4 log clearance.

By this way, clottable TgFVII/TgFVIIa was successfully immunopurified.

2.5 Ultrafiltration

As an alternative, an intermediate product that could be stored, was manufactured using the ultrafiltration technology. The affinity S/D treated eluate was concentrated and stabilized on 30 kDa Polyethersulfone membrane, single-used TangenX Sius-LS® from Novasep. Transmembrane pressure was maintained at 20 psig during the concentration phase by adjustment of the recirculating pump speed. When a protein concentration of 2 g/L was obtained, diafiltration was performed in citrate buffer to remove hydrophilic compound, salts and chemical solvents.

2.6 Sterile Filtration and Freezing—Intermediate Product 1

10.4 L of the concentrated intermediate with a specific activity of 2638 unit by mg was aseptically filtered with Sartobran® 0.45/0.2 μm capsules under a laminar flow hood into 1 L containers.

Bottles were stored <−60° C. to constitute the intermediate product for the downstream process.

2.7 Filtration 0.2/0.1 μm and Nanofiltration on 20N and 15 N Planova Filters

Further purifications were necessary for a clinical and pharmaceutical human use of the TgFVII/TgFVIIa product. Firstly, in order to reduce the potential viral load, the intermediate was filtered through the filtration train:
- 0.2/0.1 μm Sartopore 2® disposable capsule from Sartorius
- 1 sq.m Planova® 20 followed by 1 sq.m Planova® 15 from ASAHI KASEI 9.45 L intermediate was directly pumped through the filtration train at 12 LMH initial flow rate and transmembrane pressure was monitored during the entire step to maintain a maximum of 12 psig on each nanofilter. At this step of the process, the purity was calculated around 95% and endogenous transferrin was identified as one of the main contaminants.

At this stage of the process, TgFVII activation is evaluated between 20 to 50% by quantification of SDS-PAGE analysis under reduced conditions. The partial activation is attributed to the milk calcium released during the clarification phase of the purification process.

2.8 Ion Exchange Chromatography on Q Sepharose XL

Purity and activation of TgFVII was enhanced by anion exchange chromatography and calcium-dependent elution. The nanofiltered solution was loaded on a Q-Sepharose XL anion-exchanger (GE Healthcare) previously equilibrated with 10 mM sodium citrate at pH 7.0.

A first washing step was performed with 20 mM imidazole at pH 7.5 and conductivity under 5 mS/cm at 25° C. A second washing step was performed by introducing 150 mM of sodium chloride in addition to 20 mM imidazole, to reach a conductivity of 18 mS/cm at 25° C. The wash peak was identified as being mainly composed of free transferrin. The TgFVII/TgFVIIa was then eluted by decreasing the sodium chloride salt to 50 mM and in the same time by the adding calcium chloride up to 7 mM, while maintaining the imidazole at 20 mM. The elution fraction contained more than 90% of activated form of TgFVIIa evaluated by SDS-PAGE in reduced condition. RMP levels were measured by ELISA and compared to TgFVII, residual RMP was calculated below 500 ppm (see Table 3).

The QSXL chromatography contributed to the reduction of HRI levels, with a mean score of 2 $\log_{10}$, of which 1.6 $\log_{10}$ were transferrin.

During this step, activation into FVIIa was enhanced by the presence of ionized calcium in the elution buffer. Then Q-Sepharose XL eluate was stored at +2/+8° C. overnight.

2.9 Pseudo-Affinity Chromatography on Hydroxyapatite

During the storage, some FVII cleavages could occur, especially cleavage on the heavy chain, the light chain being protected by calcium ions. Hydroxyapatite and calcium phosphate adsorbants are well-known to adsorb coagulation factors such as FVII/FVIIa and more widely proteins containing Gla-domain. This pseudo-affinity was used for the polishing step of the process.

The Q Sepharose XL eluate containing the transgenic FVII/FVIIa was concentrated on a CHT Ceramic hydroxyapatite Type I column (BioRad), previously equilibrated with 25 mM Potassium phosphate at pH 8.0.

An isocratic washing step was performed with 25 mM Potassium phosphate at pH 8.0. This washing step specifically eluted proteolysed forms, especially TgFVII/TgFVIIa containing one or more cleavage on their heavy chain and was monitored to limit the minimum loss of full active forms in an isocratic mode.

The TgFVII/TgFVIIa was then eluted as a concentrate of TgFVIIa with 150 mM Potassium phosphate at pH 8.0.

2.10 Size Exclusion Chromatography (SEC) on Superdex 200

Stabilization of monomeric TgFVII/TgFVIIa was done by the last polishing step of the process. The SEC allowed the removal of potassium phosphate and the formulation into at least polysorbate 80 and arginine.

The fraction eluted from hydroxyapatite chromatographic column and containing the TgFVII/TgFVIIa was loaded on a Superdex 200 column (GE Healthcare), previously equilibrated with 5 mM Sodium citrate, 114 mM Arginine HCl, 46 mM isoleucine, 16 mM Glycine, 6.5 mM Lysine, 0.07% (v/v) Tween 80, pH 6.0.

Proteins with higher dynamic radius or higher molecular size like transferrin (70 kDa) or FVII complexed with other proteins were eluted just before the monomeric TgFVIIa (45 kDa) by size exclusion.

Proteins with lower dynamic radius or lower molecular size like caseins or peptides were eluted just after the monomeric TgFVIIa (45 kDa).

The fraction containing the TgFVII/TgFVIIa was eluted with the same buffer as used for equilibrating the column.

2.11 Stabilization and Formulation

The final TgFVII/TgFVIIa solution was formulated at a concentration of 1 g TgFVIIa/L of formulation buffer comprising 5 mM Sodium citrate, 114 mM Arginine HCl, 46 mM isoleucine, 16 mM Glycine, 6.5 mM Lysine, 0.07% (v/v) Tween 80, pH 6.0.

93.5% of activated form of TgFVIIa was evaluated by SDS-PAGE in reduced condition.

2.12 Sterilisation 5243 mL of formulated stabilized TgFVII/TgFVIIa solution were then aseptically filtered on a 0.2 μm Millipak 100 membrane.

Example 3: In Process Analytic Results

Samples generated during the purification process as described in example 2 were analyzed.

3.1 Purification Process Reproducibility.

FVII yields of each steps followed with the FVII amidolytic assay or Absorbance on 8 batches are summarized in table 1 and 2.

TABLE 1

FVII Amydolytic yields up to Ultrafiltration

| | Clarification | S/D treatment | Affinity | UFDF |
|---|---|---|---|---|
| Batch 1 | 98% | 136% | 56% | 75% |
| Batch 2 | 101% | 116% | 51% | 89% |
| Batch 3 | 95% | 120% | 54% | 91% |
| Batch 4 | 109% | 85% | N/D | N/D |
| Batch 5 | 91% | 106% | 55% | 99% |
| Batch 6 | 107% | 99% | 48% | 99% |
| Batch 7 | N/D | 83% | 47% | 86% |
| Batch 8 | 104% | 94% | 48% | 93% |
| Mean | 100% | 110% | 53% | 91% |
| SD | 7% | 18% | 3% | 10% |

N/D: No data at date

TABLE 2

FVII Absorbance yields up to sterilizing filtration

| % Step | nanofiltration | QSXL | CHT-I | SEC |
|---|---|---|---|---|
| Batch 1 | 88% | 61% | 75% | 92% |
| Batch 2 | 95% | 59% | 60% | 89% |
| Batch 3 | 95% | 63% | 52% | 92% |
| Batch 4 | 93% | 55% | 58% | 81% |
| Batch 5 | 91% | 51% | 67% | 94% |
| Batch 6 | 95% | 51% | 67% | 91% |
| Batch 7 | 92% | 49% | 49% | 86% |
| Batch 8 | 91% | 52% | 64% | 95% |
| Mean | 92% | 55% | 61% | 90% |
| SD | 3% | 5% | 9% | 5% |

FVII yields showed consistent results with less than 10% variation in regards to the mean value for each step.

3.2 RMP Clearance

Figure 2:
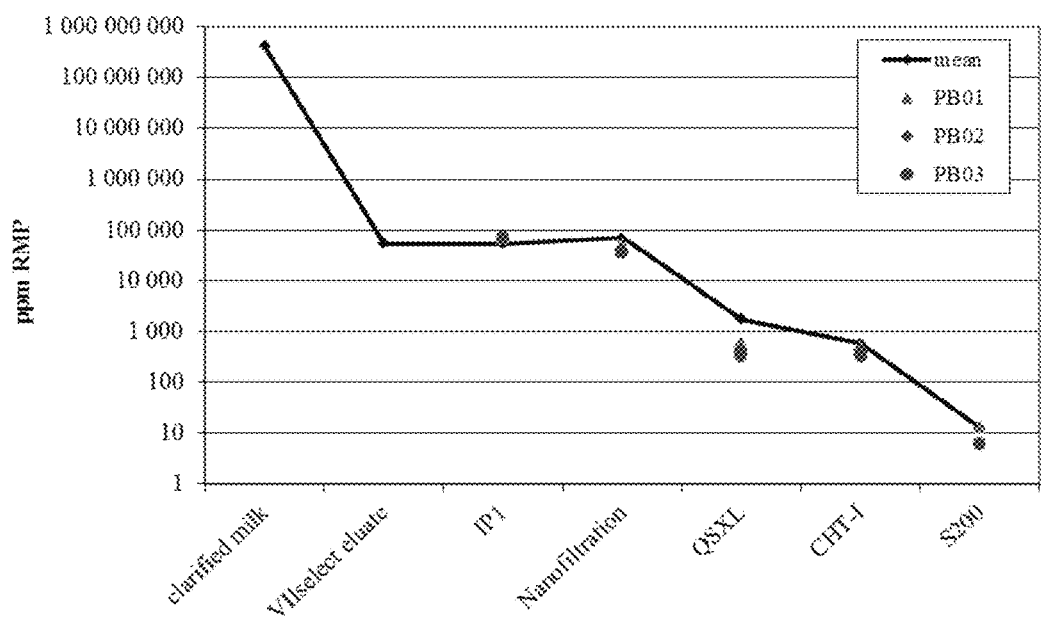

The mean RMP clearance for the tested batches was determined and is shown in FIG. 2 (RMP clearance).

RMP clearance during the purification process was perfectly reproducible. Steps that contributed the most to the RMP clearance were:
- the affinity chromatography on a ligand which is specific for FVII/FVIIa
- the Q Sepharose XL chromatography, and
- the Superdex200 chromatography.

TABLE 3

RMP clearance during the purification process.

| Mean of 3 batches | Clarified milk | Post affinity | QSXL | SEC |
|---|---|---|---|---|
| RMP in ppm | 417 731 959 | 52 356 | 1733 | 13 |

The overall RMP clearance resulting from the process was between 8 and 9 $\log_{10}$.

3.3 Rabbit DNA Clearance

Figure 3:
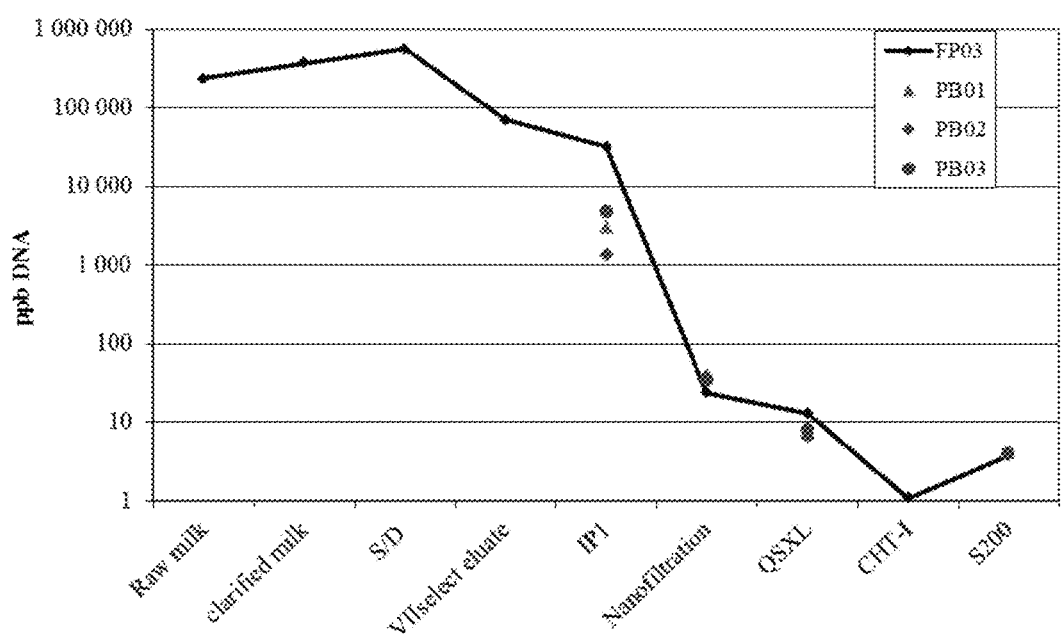

Rabbit DNA clearance was also evaluated by assaying its content in the different process intermediates by a Q-PCR technique. The corresponding results are displayed in FIG. 3 (DNA clearance). The results are expressed in ppb with respect to the TgFVII/TgFVIIa concentration assayed by ELISA in the milk and by OD280 for the other intermediates.

TABLE 4

Rabbit DNA clearance during the purification process.

| | Clarified milk | Post affinity | Nanofiltration | SEC |
|---|---|---|---|---|
| DNA in ppb | 371 134 | 69 808 | <23 | <4 |

The step that contributed the most was the nanofiltration. After the Q Sepharose XL chromatography, all batches were below the quantification level (LOQ).

The overall DNA clearance resulting from the process was between 5 and 6 $\log_{10}$.

3.4 Kinetics of FVII Activation

As disclosed above, the TgFVII activates into TgFVIIa during the process, and mainly the activation enhances with the Q Sepharose XL chromatography. As detailed in the table 5 below, at the end of the process, the activation ratio defined by the ratio of the clotting unit by antigen unit was between 17 and 25.

TABLE 5

Tg FVIIa quantification through the purification process.

| Tg FVII activation (Mean 3 PB) | Tg FVIIa | Range of Activation ratio |
|---|---|---|
| Before nanofiltration | 23,434 | 4 to 5 |
| Nanofiltrate | 16,595 | 7 to 9 |
| QSXL Eluate | 16,032 | 14 to 17 |
| CHT-I eluate | 160,822 | 17 to 25 |
| SEC Pool | 45,855 | 17 to 25 |

Figure 4:
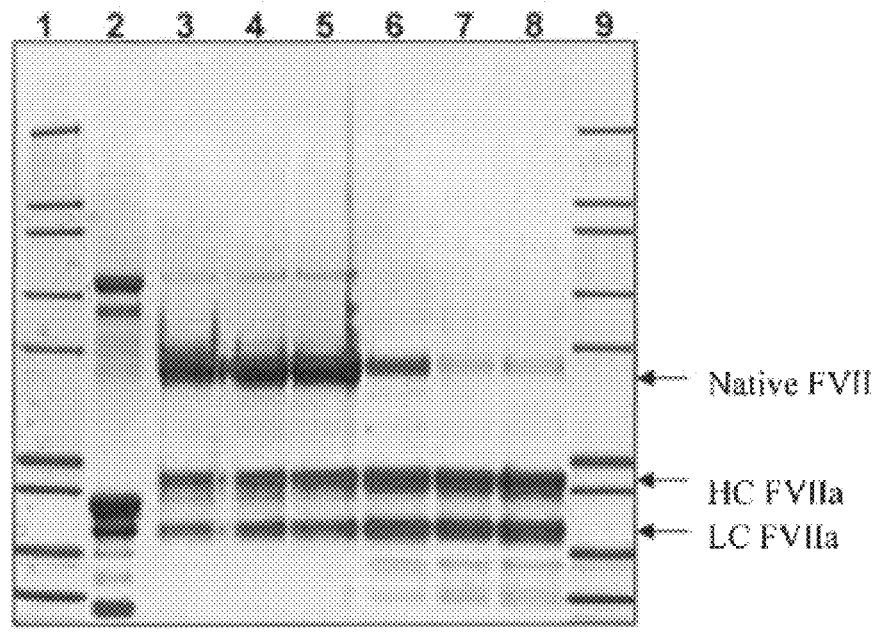

TgFVII could be roughly and easily followed by SDS-PAGE (Coomacie Blue coloration, FIG. 4)

FVII isoforms could also be quantified with a greater accuracy by Protein Mapping analysis (RP(C4)-HPLC-MS). The forms cleaved from the activation site (heavy chain and light chain) to generate biologically active TgFVIIa were determined. The uncleaved chain corresponded to non-activated TgFVII with very low biological activity and the isoforms cleaved from the light and heavy chains corresponding to molecular degradation and inactivation of the biological activity (% LC: Light Chain Cleavage or % Des-Gla, % HC: Heavy chain Cleavage).

The analytical method was not able to specifically quantify the oxidised forms. Those forms were included in the quantification of the non-activated form.

The non-activated, non degraded TgFVII decreased progressively during the process, a sign of the activation of TgFVII into TgFVIIa. For the 3 tested batches, activation was progressive and, at the end of the process, an average of 3.6% of the non-activated form remained. This form was non degraded and retained its capacity to be activated later in the process (formulation operation) and during intravenous administration. It retained its potential for activation in human plasma.

3.5 in Process TgFVIIa Degradation

For this example, the hydroxyapatite (CHT) eluate fraction was concentrated to 3.9 g/L TgFVIIa and the RP-HPLC results were summarised in table 6 in comparison to SEC results shown in table 7.

TABLE 6

FVII form repartition in the CHT eluate (RP-HPLC):

| Light chain | 28.21% |
|---|---|
| Cleaved light chain | 1.67% |
| Heavy chain | 62.29% |
| Cleaved heavy chain | 6.66% |
| Oxidized + non activated chains | 1.10% |

TABLE 7

FVII form repartition in the purified product (RP-HPLC):

| Light chain | 31.37% |
|---|---|
| Cleaved light chain | 0.48% |
| Heavy chain | 61.16% |
| Cleaved heavy chain | 5.82% |
| Oxidized + non activated chains | 1.12% |

Total of neither cleaved nor oxidized TgFVII forms was more than 90% of total TgFVII for both CHT eluate and final purified product (SEC eluate). This clearly demonstrates the ability of the CHT step to control TgFVII degradation in spite of TgFVII activation.

Example 4: Quality of the Highly Purified TgFVIIa Preparation 4.1 Residual RMP Quantification in the Purified Solution.

The use of a FVII-highly specific ligand derived from a llama antibody in combination with more classical chromatographic techniques (ion-exchange, hydroxyapatite pseudo affinity and size exclusion) thus permitted to optimize the purification of TgFVII/TgFVIIa from milk, in removing more particularly RMP as much as possible.

The RMP levels were around 10 ppm for pilot batches (15 L of milk) as depicted in table 8 and under the lower level of quantification (LLOQ) or less than 6 ng/ml for batches produced at large scale (150 L of milk).

Transferrin was assayed by ELISA in the purified product and its content was found close to 3 ppm for pilot batches.

TABLE 8

RMP and transferrin contamination in purified product

|  | RMP ppm | Transferrin ppm |
|---|---|---|
| Pilot batch 1 | 13 | 4 |
| Pilot batch 2 | <6 | 3 |
| Pilot batch 3 | <6 | 3 |
| Large scale batch 1 | <6 | N/A |

N/A: Not available 4.2 Residual Rabbit DNA Quantification in the Purified Solution.

The process as described thus reaches a target residual DNA bellow 4 ppb.

4.3 Rabbit Coagulation Factor VII

Since rabbits have an endogenous Factor VII in their circulation and there is some passive leakage of serum proteins from the blood stream into the milk the ability of the purification process to separate human for rabbit FVII was assessed. A specific ELISA was developed in-house for the investigation of the presence of such potential accompanying protein in the purified product. Results were below LLOQ (<45 pg/ml for all preparations analyzed).

Example 5: Viral Clearance Studies for Enveloped Virus (MLV, Murine Leukemia Virus) after Implementing a Step of Affinity Chromatography on Tg FVIIa Specific Ligand The characteristics of the Murine Leukemia Virus (MLV) are described in the Table below:

| Virus | MLV |
|---|---|
| Name | Murine Leukemia Virus |
| Family | Retroviridae |
| Subfamily/Genus | Orthoretrovirinae *Gammaretrovirus* |
| Natural host | Mouse |
| Genome | ARN |
| Envelope | Enveloped |
| Size in diameter | 80-110 nm |

5.1 Infectivity Titration Assay 5.1.1 Principle of Infectivity Titration

The titration method is a quantitative assay in which the virus titer measurement is based on the detection of virus production in the infected cells, by observation of a specific cytopathic effect.

The titration assay will be done on two different 96-well plates as described below:

Test sample is diluted with culture medium by serial 3-fold dilutions (eight replicates are performed for each dilution) across the 96-well plate ("sample dilution plate").

Each well from the "sample dilution plate" is then inoculated on the corresponding well of a new 96-well plate ("sample titration plate").

Cell suspension is added to each well of the "sample titration plate" and the plates are then incubated at appropriate temperature with or without $CO_2$ atmosphere (depending on viruses).

After a period of incubation allowing viral replication and infection of adjacent cells, depending on viruses, wells with foci are counted after infection by observation under inverted light microscope.

or a stain overlay (crystal violet 1p-Galactosidase) is added and wells are examined for cytopathic effect. The infected wells show up as clear areas whereas the non-infected wells are stained (or the other way round depending on viruses).

The infectious titer expressed as 50% tissue culture infective dose per milliliter ($TCID_{50}$/mL) is calculated using the appropriate formula.

5.1.2 Titration Controls

Negative Control

During each titration assay, cells are prepared as cell reference control. These cells are prepared in the same conditions as those used for the titration of the samples generated during the preliminary assays except that they are inoculated with unspiked culture medium (4-8 wells in each 96 wells plate).

Positive Titration Control (Virus Reference Control)

During each titration assay, a virus reference control of approximately $10^3$-$10^5$ $TCID_{50}$/mL is titrated in the same conditions as those used for the titration of the samples generated during the preliminary assays.

5.1.3 Acceptance Criteria of the Titration Assay

The titration assay is retained and validated when:

The cell reference control for each titration plate is conform to the expected result, The infectious titer of the virus reference control obtained is in the expected range.

5.1.4. Determination of the Viral Titer

The viral titer is determinated according to Schwartz D., 1993 (Schwartz D., "Méthodes statistiques à l'usage des médecins et des biologistes", Flammarion Médecine-Sciences, fourth edition, 1993); Kaplan M. and Koprowski H., "Laboratory techniques in rabies, third edition, edited by World Health Organization, Geneva, 1973.

The $TCID_{50}$ (50% Tissue Culture Infective Dose) is calculated using Spearman Karber formula. The $TCID_{50}$ is evaluated by quantal assay and defined as the virus dose capable of infecting 50% of the inoculated cultures.

5.2 Experimental Protocol

The steps implemented in the process are as follows:

Thawing of the clarified source material;

Infection of the thawed clarified source material with 1% of the enveloped virus MLV;

Prefiltration with filters 0.2 µm;

Loading onto the FVII Select column;

Column washing;

Elution.

Table 9 provides process conditions implemented during the step of affinity FVII Select chromatography.

TABLE 9

| OPERATING PARAMETERS | FULL SCALE CONDITIONS | VIRAL CLEARANCE CONDITIONS |
|---|---|---|
| Column characteristics | | |
| Column type | Radial | Radial |
| Gel (resin) reference | Affinity Select VII* | Affinity Select VII* |
| Chromatography parameters | | |
| Load volume | 846 L | 0.282 L |
|  | (56.4 L/L of gel) | (56.4 L/L of gel) |
| Protein load | ≈39.6 g | ≈5.1 g/L of gel |
|  | (≈5.1 g/L of gel) | |
| Chromatography flow rate | 480 L/h | 0.16 L/h |

*Affinity Select VII gel identical to affinity gel used in example 2.4

5.3 Results

Viral clearance has been measured in a sample of thawed and clarified source material after the step of prefiltration (sample named Load 2) and after elution on affinity FVII Select chromatography (sample named Eluate). Results are shown in Table 10.

TABLE 10

Measurement of viral clearance before (Load 2) and after affinity FVII Select chromatography (Eluate)

| | Load 2 | | | Eluate | | | |
|---|---|---|---|---|---|---|---|
| Virus | Titer ($\log_{10}$ $TCID_{50}$/ml) | Volume (ml) | Total input ($\log_{10}$ $TCID_{50}$) | Titer ($\log_{10}$ $TCID_{50}$/ml) | Volume (ml) | Total output ($\log_{10}$ $TCID_{50}$) | Reduction factor ($\log_{10}$) |
| MLV | 5.48 | 282 | 7.93 | <1.84 | 52 | <3.56 | >4.37 |

$TCID_{50}$: 50% tissue culture infective dose

Results of Table 10 show that the Affinity FVII Select chromatography step reduces the viral titer of a reduction factor (RF) superior to 4.37 $\log_{10}$.

Example 6: Viral Clearance Studies for Non-Enveloped Virus (PPV, Porcine ParvoVirus) after Implementing a Step of Affinity Chromatography on Tg FVIIa Specific Ligand The characteristics of the Porcine ParvoVirus (PPV) are described in the Table below:

| Virus | PPV |
|---|---|
| Strain | NADL-2 strain |
| Name | Porcine ParvoVirus |
| Family | Parvoviridae |
| Subfamily/Genus | Parvovirinae/Parvovirus |
| Natural host | Porcine |
| Genome | Single-stranded DNA |
| Envelope | Naked |
| Size in diameter | 18-24 nm |

6.1 Experimental Protocol

The steps implemented in the process are as follows:
Thawing of the clarified source material;
Infection of the thawed clarified source material with 1% of the non-enveloped virus PPV;
Prefiltration with filters 0.65/0.45 μm and 0.45/0.2 μm;
Solvent/detergent treatment (1 hour);
Loading onto the FVII Select column;
Washing;
Elution.

Table 11 provides process conditions implemented during the step of affinity FVII Select chromatography.

| OPERATING PARAMETERS | FULL SCALE CONDITIONS | VIRAL CLEARANCE CONDITIONS |
|---|---|---|
| | Column characteristics | |
| Column type | Radial | Radial |
| Gel (resin) reference | Affinity Select VII* | Affinity Select VII* |
| | Chromatography parameters | |
| Load volume | ≈918 L | 0.31 L |
| | (≈61 L/L of gel) | (62 L/L of gel) |
| Protein load | ≈5.3 g/L of gel | ≈5.3 g/L of gel |
| Chromatography flow rate | 480 L/h | 0.16 L/h |

*Affinity Select VII gel identical to affinity gel used in example 2.4

6.2 Results

Viral clearance has been measured in a sample of thawed and clarified source material after the step of prefiltration and of solvent/detergent treatment (sample named Initial Load) and after elution on affinity FVII Select chromatography (sample named Eluate A). Results are shown under histogram form in FIG. 5.

Figure 5:
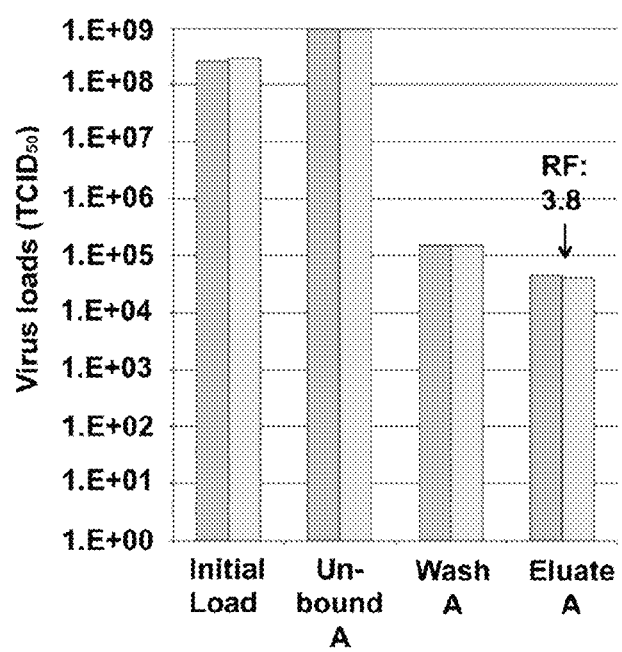

Histogram of FIG. 5 shows that the Affinity FVII Select chromatography step reduces the viral titer of a reduction factor (RF) superior to 3.8 $\log_{10}$.

Example 7: Viral Clearance Studies for Enveloped Virus (MLV) and Non-Enveloped Virus (PPV) after Implementing a Step of Size Exclusion Chromatography Superdex S200 Prep Grad

7.1 Experimental Protocol

The steps implemented in the process are as follows:
Thawing of the starting material sampled from clinical batches (ceramic hydroxyapatite-1 (CHT-1) eluate);
Infection of the starting material with 1% of spike (1% MLV or 1% of PPV);
Prefiltration with filters 0.2 μm (MLV) or filters 0.1 μm (PPV);
Loading 2.3% column volume (CV) onto the S200 column;
Collect of the S200 eluate (fraction corresponding to FVII).

Table 12 provides process conditions implemented during the step of size exclusion chromatography Superdex S200 prep grad.

| OPERATING PARAMETERS | FULL SCALE CONDITIONS 1X | FULL SCALE CONDITIONS 4X | VIRAL CLEARANCE CONDITIONS |
|---|---|---|---|
| | COLUMN CHARACTERISTICS | | |
| Column type | BPG300 | Axichrom450 | Valichrom 11 - Atoll |
| Gel (resin) reference | Superdex S200* | Superdex S200* | Superdex S200* |
| | CHROMATOGRAPHY PARAMETERS | | |
| Load volume | 2.3% CV (1.57 L (mean), [1.47-1.65]) | 2.3% CV (3.5 L) | 2.3% CV (2.3 mL) |
| Chromatography flow rate | 16 L/h | 36 L/h | 0.16 L/h |

**Superdex S200 gel identical to gel used in example 2.10

7.2 Results

Viral clearance has been measured in a sample of CHT-1 eluate after the step of prefiltration on filters 0.2 μm (for MLV virus) or on filters 0.1 μm (for PPV virus) (sample named Load 2), and after elution on size exclusion chromatography Superdex S200 (sample named Eluate). Results are shown in Table 13.

TABLE 13

Measurement of viral clearance before (Load 2) and after size exclusion chromatography Superdex S200 (Eluate)

| | Load 2 | | | Eluate | | | |
|---|---|---|---|---|---|---|---|
| Virus | Titer ($\log_{10}$ $TCID_{50}$/ ml) | Volume (ml) | Total input ($\log_{10}$ $TCID_{50}$) | Titer ($\log_{10}$ $TCID_{50}$/ ml) | Volume (ml) | Total output ($\log_{10}$ $TCID_{50}$) | Reduction factor ($\log_{10}$) |
| MLV | 5.48 | 2.3 | 5.84 | 1.84* | 9.80 | 2.83 | 3.01 |
| PPV | 6.01 | 2.3 | 6.37 | 2.52** | 7.17 | 3.38 | 3.00 |

$TCID_{50}$: 50% tissue culture infective dose

Results of Table 10 show that the size exclusion chromatography Superdex S200 chromatography reduces the viral titer of a reduction factor equal to 3.01 $\log_{10}$ for enveloped virus (MLV) and a reduction factor equal to 3.00 $\log_{10}$ for non-enveloped virus (PPV).

In summary:

High reduction factors of viral clearance are obtained with the affinity FVII Select chromatography, which are superior to 4.37 $\log_{10}$ for enveloped virus (MLV) and equal to 3.8 $\log_{10}$ for non-enveloped virus (PPV);

Medium reduction factors of viral clearance are obtained with the size exclusion chromatography Superdex S200, which are equal to 3.0 $\log_{10}$ for enveloped virus (MLV) and non-enveloped virus (PPV); The affinity FVII Select chromatography is more efficient than the size exclusion chromatography Superdex S200 for reducing the viral titer of enveloped and non-enveloped viruses.

Example 8: Viral Clearance Studies for Enveloped Virus and Non-Enveloped Virus after Implementing Several Technics 8.1 Experimental Protocol FVII Select affinity chromatography, nanofiltration and Q Sepharose XL viral validation studies were performed separately with 1% spiking of various viruses in the starting material for each purification unit operation and titration of the spiked virus in the fraction of interest (the one were FVII is recovered). $\log_{10}$ Reduction Factor obtained for each purification unit operation were added for each virus and a global reduction factor was estimated virus by virus.

8.2 Results

Results are given in Table 14.

TABLE 14

| | Spiked Viruses | | | | |
|---|---|---|---|---|---|
| | Enveloped Viruses | | | Non-Enveloped Viruses | |
| | | | | FCV | |
| Model for | MLV Retroviruses | BVDV Resistant Species Among EV | PRV Herpes viruses, Epstein Barr virus | HEV, RHDV, other medium-sized NEV | PPV Parvoviruses, resistant very small NEV |
| FVII Select chromatography | >4.4 | NA | NA | NA | 3.8 |
| Solvent/detergent treatment | >5.2 | >4.5 | >5.9 | NE | NE |
| Nanofiltration | ≥4.0 | ≥4.4 | NA | ≥4.6 | 6.0 |
| Solvent/detergent treatment + Nanofiltration | ≥9.2 | ≥8.9 | NA | ≥4.6 | 6.0 |
| QSXL chromatography* | ≥4.9 | 2.9 | ≥5.1 | 5.3 | 6.7 |
| Estimated global reduction factor (RF) | >18.5 | >11.8 | >11.0 | >9.9 | 16.5 |

*Identical to the ion exchange chromatography step of example 2.8
NA: Not available
NE: Not effective. The solvent-detergent treatment is not effective on non-enveloped viruses.

Table 14 shows that:

The implementation of FVII Select chromatography step plus nanofiltration plus Q Sepharose XL ion exchange chromatography step in the process conduct to an increase of viral reduction by 9.3 $\log_{10}$ leading to a global reduction factor for non-enveloped viruses greater or equal than 18.5 $\log_{10}$ for PPV viral model The implementation of FVII Select chromatography step plus nanofiltration plus Q Sepharose XL ion exchange chromatography step in the process conduct to an increase of viral reduction by 10.5 $\log_{10}$ leading to a to a global reduction factor for enveloped viruses equal to 16.5 $\log_{10}$ with MLV viral model

The invention claimed is:

1. A method for purifying human transgenic Factor VII (TgFVII) and/or human transgenic activated Factor VII (TgFVIIa) produced in milk of a transgenic female rabbit, comprising the steps of:
   (a) affinity chromatography, comprising
      (i) contacting the milk containing human TgFVII and/or human TgFVIIa with a ligand which is specific to human TgFVII and/or human TgFVIIa, under conditions allowing the human TgFVII and/or human TgFVIIa to bind the ligand, and
      (ii) eluting human TgFVII and/or human TgFVIIa by disrupting the interaction with said ligand, wherein TgFVII and/or TgFVIIa activity is retained,
   wherein the ligand is an antigen-binding protein directed to at least one human TgFVII or human TgFVIIa epitope, the ligand is devoid of light polypeptide chains, and the ligand is obtained from heavy immunoglobulin chains of Camelidae;

(b) chromatographic purification of the eluted human TgFVII and/or human TgFVIIa on an ion exchanger, under conditions wherein human TgFVII and/or human TgFVIIa are retained on the ion exchanger;

(c) chromatographic separation of the eluted human TgFVII and/or human TgFVIIa on pseudo-affinity resin, under conditions wherein human TgFVII and/or human TgFVIIa are retained on the pseudo-affinity resin; and (d) chromatographic separation of the eluted human TgFVII and/or human TgFVIIa on a size exclusion support.

2. The method of claim 1, wherein said ligand comprises two heavy polypeptide chains forming two complete antigen binding sites.

3. The method of claim 1, wherein step (a) further comprises at least one washing step for removing unbound material and weakly bound material before step (ii) eluting the human TgFVII or human TgFVIIa from the ligand.

4. The method of claim 1, further comprising preliminary steps, before step (a), of collecting and clarifying the milk.

5. The method of claim 4, wherein the clarifying the milk step is performed by citrate salt addition, followed by filtration.

6. The method of claim 1, further comprising at least one step of eliminating and/or inactivating viruses.

7. The method of claim 1, further comprising steps of formulating, sterilizing and lyophilizing the purified human TgFVII and/or human TgFVIIa.

8. The method of claim 3, wherein the at least one washing step is performed with a buffer comprising from 10% to 50% of a hydrophobic agent, the ionic strength of which ranges from 200 to 600 mM.

9. The method of claim 3, wherein, eluting the human TgFVII and/or human TgFVIIa from the resin is performed with a buffer comprising from 20% to 70% of a hydrophobic agent, the ionic strength of which ranges from 500 to 2500 mM.

10. The method of claim 1, wherein the resulting purified human transgenic FVII is activated, high purity human FVII, comprising a low percentage of degraded, proteolyzed or oxidized forms.

11. The method of claim 1, wherein the method achieves a viral reduction factor superior to 3 $\log_{10}$, superior to 4 $\log_{10}$, or superior to 5 $\log_{10}$.

12. The method of claim 1, wherein the ion exchanger is an anion exchanger.

13. The method of claim 1, wherein the pseudo-affinity resin is hydroxyapatite.

14. The method of claim 6, wherein the at least one step of eliminating and/or inactivating viruses comprises nanofiltration and/or solvent/detergent treatment.

15. The method of claim 1, wherein the antigen-binding protein has a kinetic binding constant to the human TgFVII or human TgFVIIa epitope of $Ka=2.58\times10^{8}$ and $Kd=9.88\times10^{-9}$.

16. The method of claim 1, wherein the ligand has an affinity of from 1 to nM for the transgenic human TgFVII or human TgFVIIa.

17. The method of claim 1, wherein the ligand is obtained from heavy immunoglobulin chains of Camelidae selected from the group consisting of *Camelus bactrianus, Camelus dromedarius, Lama pacos, Lama glama* and *Lama vicugna.*

* * * * *

SEQUENCE LISTING

<160> NUMBER OF SEQ ID NOS: 41

<210> SEQ ID NO 1
<211> LENGTH: 22
<212> TYPE: PRT
<213> ORGANISM: artificial sequences
<220> FEATURE:
<221> NAME/KEY: SOURCE
<222> LOCATION: 1..22
<223> OTHER INFORMATION: /mol_type="protein"
      /note="Antigen-Binding protein Framework 1 domain"
      /organism="artificial sequences"

<400> SEQUENCE: 1

Gly Gly Ser Val Gln Thr Gly Gly Ser Leu Arg Leu Ser Cys Glu Ile
1               5                   10                  15

Ser Gly Leu Thr Phe Asp
            20

<210> SEQ ID NO 2
<211> LENGTH: 22
<212> TYPE: PRT
<213> ORGANISM: artificial sequences
<220> FEATURE:
<221> NAME/KEY: SOURCE
<222> LOCATION: 1..22
<223> OTHER INFORMATION: /mol_type="protein"
      /note="Antigen-Binding protein Framework 1 domain"
      /organism="artificial sequences"

<400> SEQUENCE: 2

Gly Gly Ser Val Gln Thr Gly Gly Ser Leu Arg Leu Ser Cys Ala Val
1               5                   10                  15

Ser Gly Phe Ser Phe Ser
            20

<210> SEQ ID NO 3
<211> LENGTH: 22
<212> TYPE: PRT
<213> ORGANISM: artificial sequences
<220> FEATURE:
<221> NAME/KEY: SOURCE
<222> LOCATION: 1..22
<223> OTHER INFORMATION: /mol_type="protein"
      /note="Antigen-Binding protein Framework 1 domain"
      /organism="artificial sequences"

<400> SEQUENCE: 3

Gly Gly Ser Glu Gln Gly Gly Gly Ser Leu Arg Leu Ser Cys Ala Ile
1               5                   10                  15

Ser Gly Tyr Thr Tyr Gly
            20

<210> SEQ ID NO 4
<211> LENGTH: 22
<212> TYPE: PRT
<213> ORGANISM: artificial sequences
<220> FEATURE:
<221> NAME/KEY: SOURCE
<222> LOCATION: 1..22
<223> OTHER INFORMATION: /mol_type="protein"
      /note="Antigen-Binding protein Framework 1 domain"
      /organism="artificial sequences"

<400> SEQUENCE: 4

Gly Gly Ser Val Gln Pro Gly Gly Ser Leu Thr Leu Ser Cys Thr Val
1               5                   10                  15

Ser Gly Ala Thr Tyr Ser
            20

<210> SEQ ID NO 5
<211> LENGTH: 22
<212> TYPE: PRT
<213> ORGANISM: artificial sequences
<220> FEATURE:
<221> NAME/KEY: SOURCE
<222> LOCATION: 1..22
<223> OTHER INFORMATION: /mol_type="protein"
      /note="Antigen-Binding protein Framework 1 domain"
      /organism="artificial sequences"

<400> SEQUENCE: 5

Gly Gly Ser Val Gln Ala Gly Gly Ser Leu Arg Leu Ser Cys Thr Gly
1               5                   10                  15

Ser Gly Phe Pro Tyr Ser
            20

<210> SEQ ID NO 6
<211> LENGTH: 21
<212> TYPE: PRT
<213> ORGANISM: artificial sequences
<220> FEATURE:
<221> NAME/KEY: SOURCE
<222> LOCATION: 1..21
<223> OTHER INFORMATION: /mol_type="protein"
      /note="Antigen-Binding protein Framework 1 domain"
      /organism="artificial sequences"

<400> SEQUENCE: 6

Gly Gly Ser Val Gln Ala Gly Gly Ser Leu Arg Leu Ser Cys Val Ala
1               5                   10                  15

Gly Phe Gly Thr Ser
            20

<210> SEQ ID NO 7
<211> LENGTH: 21
<212> TYPE: PRT
<213> ORGANISM: artificial sequences
<220> FEATURE:
<221> NAME/KEY: SOURCE
<222> LOCATION: 1..21
<223> OTHER INFORMATION: /mol_type="protein"
      /note="Antigen-Binding protein Framework 1 domain"
      /organism="artificial sequences"

<400> SEQUENCE: 7

Gly Gly Ser Val Gln Ala Gly Gly Ser Leu Arg Leu Ser Cys Val Ser
1               5                   10                  15

Phe Ser Pro Ser Ser
            20

<210> SEQ ID NO 8
<211> LENGTH: 11
<212> TYPE: PRT
<213> ORGANISM: artificial sequences
<220> FEATURE:
<221> NAME/KEY: SOURCE
<222> LOCATION: 1..11
<223> OTHER INFORMATION: /mol_type="protein"
      /note="Antigen-Binding protein Framework 4 domain"
      /organism="artificial sequences"

<400> SEQUENCE: 8

Trp Gly Gln Gly Thr Gln Val Thr Val Ser Ser
1               5                   10

```
<210> SEQ ID NO 9
<211> LENGTH: 11
<212> TYPE: PRT
<213> ORGANISM: artificial sequences
<220> FEATURE:
<221> NAME/KEY: SOURCE
<222> LOCATION: 1..11
<223> OTHER INFORMATION: /mol_type="protein"
      /note="Antigen-Binding protein Framework 4 domain"
      /organism="artificial sequences"

<400> SEQUENCE: 9

Trp Gly Gln Gly Thr Leu Val Thr Val Ser Ser
1               5                   10

<210> SEQ ID NO 10
<211> LENGTH: 11
<212> TYPE: PRT
<213> ORGANISM: artificial sequences
<220> FEATURE:
<221> NAME/KEY: SOURCE
<222> LOCATION: 1..11
<223> OTHER INFORMATION: /mol_type="protein"
      /note="Antigen-Binding protein Framework 4 domain"
      /organism="artificial sequences"

<400> SEQUENCE: 10

Trp Gly Gln Gly Ala Gln Val Thr Val Ser Ser
1               5                   10

<210> SEQ ID NO 11
<211> LENGTH: 11
<212> TYPE: PRT
<213> ORGANISM: artificial sequences
<220> FEATURE:
<221> NAME/KEY: SOURCE
<222> LOCATION: 1..11
<223> OTHER INFORMATION: /mol_type="protein"
      /note="Antigen-Binding protein Framework 4 domain"
      /organism="artificial sequences"

<400> SEQUENCE: 11

Trp Gly Gln Gly Thr Gln Val Thr Ala Ser Ser
1               5                   10

<210> SEQ ID NO 12
<211> LENGTH: 11
<212> TYPE: PRT
<213> ORGANISM: artificial sequences
<220> FEATURE:
<221> NAME/KEY: SOURCE
<222> LOCATION: 1..11
<223> OTHER INFORMATION: /mol_type="protein"
      /note="Antigen-Binding protein Framework 4 domain"
      /organism="artificial sequences"

<400> SEQUENCE: 12

Arg Gly Gln Gly Thr Gln Val Thr Val Ser Leu
1               5                   10

<210> SEQ ID NO 13
<211> LENGTH: 14
<212> TYPE: PRT
<213> ORGANISM: artificial sequences
<220> FEATURE:
<221> NAME/KEY: SOURCE
<222> LOCATION: 1..14
<223> OTHER INFORMATION: /mol_type="protein"
      /note="Antigen-Binding protein CDR3 domain"
```

```
        /organism="artificial sequences"
<220> FEATURE:
<221> NAME/KEY: MOD_RES
<222> LOCATION: 12
<223> OTHER INFORMATION: Xaa can be any naturally occuring amino acid

<400> SEQUENCE: 13

Ala Leu Gln Pro Gly Gly Tyr Cys Gly Tyr Gly Xaa Cys Leu
1               5                   10

<210> SEQ ID NO 14
<211> LENGTH: 12
<212> TYPE: PRT
<213> ORGANISM: artificial sequences
<220> FEATURE:
<221> NAME/KEY: SOURCE
<222> LOCATION: 1..12
<223> OTHER INFORMATION: /mol_type="protein"
        /note="Antigen-Binding protein CDR3 domain"
        /organism="artificial sequences"

<400> SEQUENCE: 14

Val Ser Leu Met Asp Arg Ile Ser Gln His Gly Cys
1               5                   10

<210> SEQ ID NO 15
<211> LENGTH: 18
<212> TYPE: PRT
<213> ORGANISM: artificial sequences
<220> FEATURE:
<221> NAME/KEY: SOURCE
<222> LOCATION: 1..18
<223> OTHER INFORMATION: /mol_type="protein"
        /note="Antigen-Binding protein CDR3 domain"
        /organism="artificial sequences"

<400> SEQUENCE: 15

Val Pro Ala His Leu Gly Pro Gly Ala Ile Leu Asp Leu Lys Lys Tyr
1               5                   10                  15

Lys Tyr

<210> SEQ ID NO 16
<211> LENGTH: 15
<212> TYPE: PRT
<213> ORGANISM: artificial sequences
<220> FEATURE:
<221> NAME/KEY: SOURCE
<222> LOCATION: 1..15
<223> OTHER INFORMATION: /mol_type="protein"
        /note="Antigen-Binding protein CDR3 domain"
        /organism="artificial sequences"

<400> SEQUENCE: 16

Phe Cys Tyr Ser Thr Ala Gly Asp Gly Gly Ser Gly Glu Met Tyr
1               5                   10                  15

<210> SEQ ID NO 17
<211> LENGTH: 15
<212> TYPE: PRT
<213> ORGANISM: artificial sequences
<220> FEATURE:
<221> NAME/KEY: SOURCE
<222> LOCATION: 1..15
<223> OTHER INFORMATION: /mol_type="protein"
        /note="Antigen-Binding protein CDR3 domain"
        /organism="artificial sequences"

<400> SEQUENCE: 17

Glu Leu Ser Gly Gly Ser Cys Glu Leu Pro Leu Leu Phe Asp Tyr
```

```
<210> SEQ ID NO 18
<211> LENGTH: 17
<212> TYPE: PRT
<213> ORGANISM: artificial sequences
<220> FEATURE:
<221> NAME/KEY: SOURCE
<222> LOCATION: 1..17
<223> OTHER INFORMATION: /mol_type="protein"
      /note="Antigen-Binding protein CDR3 domain"
      /organism="artificial sequences"

<400> SEQUENCE: 18

Asp Trp Lys Tyr Trp Thr Cys Gly Ala Gln Thr Gly Gly Tyr Phe Gly
1               5                   10                  15

Gln

<210> SEQ ID NO 19
<211> LENGTH: 24
<212> TYPE: PRT
<213> ORGANISM: artificial sequences
<220> FEATURE:
<221> NAME/KEY: SOURCE
<222> LOCATION: 1..24
<223> OTHER INFORMATION: /mol_type="protein"
      /note="Antigen-Binding protein CDR3 domain"
      /organism="artificial sequences"

<400> SEQUENCE: 19

Arg Leu Thr Glu Met Gly Ala Cys Asp Ala Arg Trp Ala Thr Leu Ala
1               5                   10                  15

Thr Arg Thr Phe Ala Tyr Asn Tyr
            20

<210> SEQ ID NO 20
<211> LENGTH: 16
<212> TYPE: PRT
<213> ORGANISM: artificial sequences
<220> FEATURE:
<221> NAME/KEY: SOURCE
<222> LOCATION: 1..16
<223> OTHER INFORMATION: /mol_type="protein"
      /note="Antigen-Binding protein CDR3 domain"
      /organism="artificial sequences"

<400> SEQUENCE: 20

Gln Lys Lys Asp Arg Thr Arg Trp Ala Glu Pro Arg Glu Trp Asn Asn
1               5                   10                  15

<210> SEQ ID NO 21
<211> LENGTH: 21
<212> TYPE: PRT
<213> ORGANISM: artificial sequences
<220> FEATURE:
<221> NAME/KEY: SOURCE
<222> LOCATION: 1..21
<223> OTHER INFORMATION: /mol_type="protein"
      /note="Antigen-Binding protein CDR3 domain"
      /organism="artificial sequences"

<400> SEQUENCE: 21

Gly Ser Arg Phe Ser Ser Pro Val Gly Ser Thr Ser Arg Leu Glu Ser
1               5                   10                  15

Ser Asp Tyr Asn Tyr
            20
```

```
<210> SEQ ID NO 22
<211> LENGTH: 16
<212> TYPE: PRT
<213> ORGANISM: artificial sequences
<220> FEATURE:
<221> NAME/KEY: SOURCE
<222> LOCATION: 1..16
<223> OTHER INFORMATION: /mol_type="protein"
      /note="Antigen-Binding protein CDR3 domain"
      /organism="artificial sequences"
<220> FEATURE:
<221> NAME/KEY: MOD_RES
<222> LOCATION: 11
<223> OTHER INFORMATION: Xaa can be any naturally occuring amino acid

<400> SEQUENCE: 22

Ala Asp Pro Ser Ile Tyr Tyr Ser Ile Leu Xaa Ile Glu Tyr Lys Tyr
1               5                   10                  15

<210> SEQ ID NO 23
<211> LENGTH: 22
<212> TYPE: PRT
<213> ORGANISM: artificial sequences
<220> FEATURE:
<221> NAME/KEY: SOURCE
<222> LOCATION: 1..22
<223> OTHER INFORMATION: /mol_type="protein"
      /note="Antigen-Binding protein CDR3 domain"
      /organism="artificial sequences"

<400> SEQUENCE: 23

Asp Ser Pro Cys Tyr Met Pro Thr Met Pro Ala Pro Pro Ile Arg Asp
1               5                   10                  15

Ser Phe Gly Trp Asp Asp
            20

<210> SEQ ID NO 24
<211> LENGTH: 15
<212> TYPE: PRT
<213> ORGANISM: artificial sequences
<220> FEATURE:
<221> NAME/KEY: SOURCE
<222> LOCATION: 1..15
<223> OTHER INFORMATION: /mol_type="protein"
      /note="Antigen-Binding protein CDR3 domain"
      /organism="artificial sequences"

<400> SEQUENCE: 24

Thr Ser Ser Phe Tyr Trp Tyr Cys Thr Thr Ala Pro Tyr Asn Val
1               5                   10                  15

<210> SEQ ID NO 25
<211> LENGTH: 16
<212> TYPE: PRT
<213> ORGANISM: artificial sequences
<220> FEATURE:
<221> NAME/KEY: SOURCE
<222> LOCATION: 1..16
<223> OTHER INFORMATION: /mol_type="protein"
      /note="Antigen-Binding protein CDR3 domain"
      /organism="artificial sequences"

<400> SEQUENCE: 25

Thr Glu Ile Glu Trp Tyr Gly Cys Asn Leu Arg Thr Thr Phe Thr Arg
1               5                   10                  15

<210> SEQ ID NO 26
<211> LENGTH: 22
<212> TYPE: PRT
<213> ORGANISM: artificial sequences
```

```
<220> FEATURE:
<221> NAME/KEY: SOURCE
<222> LOCATION: 1..22
<223> OTHER INFORMATION: /mol_type="protein"
      /note="Antigen-Binding protein CDR3 domain"
      /organism="artificial sequences"

<400> SEQUENCE: 26

Asn Gln Leu Ala Gly Gly Trp Tyr Leu Asp Pro Asn Tyr Trp Leu Ser
1               5                   10                  15

Val Gly Ala Tyr Ala Ile
            20

<210> SEQ ID NO 27
<211> LENGTH: 24
<212> TYPE: PRT
<213> ORGANISM: artificial sequences
<220> FEATURE:
<221> NAME/KEY: SOURCE
<222> LOCATION: 1..24
<223> OTHER INFORMATION: /mol_type="protein"
      /note="Antigen-Binding protein CDR3 domain"
      /organism="artificial sequences"

<400> SEQUENCE: 27

Arg Leu Thr Glu Met Gly Ala Cys Asp Ala Arg Trp Ala Thr Leu Ala
1               5                   10                  15

Thr Arg Thr Phe Ala Tyr Asn Tyr
            20

<210> SEQ ID NO 28
<211> LENGTH: 24
<212> TYPE: PRT
<213> ORGANISM: artificial sequences
<220> FEATURE:
<221> NAME/KEY: SOURCE
<222> LOCATION: 1..24
<223> OTHER INFORMATION: /mol_type="protein"
      /note="Antigen-Binding protein CDR3 domain"
      /organism="artificial sequences"

<400> SEQUENCE: 28

Asp Gly Trp Thr Arg Lys Glu Gly Gly Ile Gly Leu Pro Trp Ser Val
1               5                   10                  15

Gln Cys Glu Asp Gly Tyr Asn Tyr
            20

<210> SEQ ID NO 29
<211> LENGTH: 10
<212> TYPE: PRT
<213> ORGANISM: artificial sequences
<220> FEATURE:
<221> NAME/KEY: SOURCE
<222> LOCATION: 1..10
<223> OTHER INFORMATION: /mol_type="protein"
      /note="Antigen-Binding protein CDR3 domain"
      /organism="artificial sequences"

<400> SEQUENCE: 29

Asp Ser Tyr Pro Cys His Leu Leu Asp Val
1               5                   10

<210> SEQ ID NO 30
<211> LENGTH: 12
<212> TYPE: PRT
<213> ORGANISM: artificial sequences
<220> FEATURE:
<221> NAME/KEY: SOURCE
```

<222> LOCATION: 1..12
<223> OTHER INFORMATION: /mol_type="protein"
      /note="Antigen-Binding protein CDR3 domain"
      /organism="artificial sequences"

<400> SEQUENCE: 30

Val Glu Tyr Pro Ile Ala Asp Met Cys Ser Arg Tyr
1               5                   10

<210> SEQ ID NO 31
<211> LENGTH: 27
<212> TYPE: PRT
<213> ORGANISM: artificial sequences
<220> FEATURE:
<221> NAME/KEY: SOURCE
<222> LOCATION: 1..27
<223> OTHER INFORMATION: /mol_type="protein"
      /note="Antigen-Binding protein CH2 domain"
      /organism="artificial sequences"

<400> SEQUENCE: 31

Ala Pro Glu Leu Leu Gly Gly Pro Thr Val Phe Ile Phe Pro Pro Lys
1               5                   10                  15

Pro Lys Asp Val Leu Ser Ile Thr Leu Thr Pro
            20                  25

<210> SEQ ID NO 32
<211> LENGTH: 27
<212> TYPE: PRT
<213> ORGANISM: artificial sequences
<220> FEATURE:
<221> NAME/KEY: SOURCE
<222> LOCATION: 1..27
<223> OTHER INFORMATION: /mol_type="protein"
      /note="Antigen-Binding protein CH2 domain"
      /organism="artificial sequences"

<400> SEQUENCE: 32

Ala Pro Glu Leu Pro Gly Gly Pro Ser Val Phe Val Phe Pro Thr Lys
1               5                   10                  15

Pro Lys Asp Val Leu Ser Ile Ser Gly Arg Pro
            20                  25

<210> SEQ ID NO 33
<211> LENGTH: 27
<212> TYPE: PRT
<213> ORGANISM: artificial sequences
<220> FEATURE:
<221> NAME/KEY: SOURCE
<222> LOCATION: 1..27
<223> OTHER INFORMATION: /mol_type="protein"
      /note="Antigen-Binding protein CH2 domain"
      /organism="artificial sequences"

<400> SEQUENCE: 33

Ala Pro Glu Leu Pro Gly Gly Pro Ser Val Phe Val Phe Pro Pro Lys
1               5                   10                  15

Pro Lys Asp Val Leu Ser Ile Ser Gly Arg Pro
            20                  25

<210> SEQ ID NO 34
<211> LENGTH: 27
<212> TYPE: PRT
<213> ORGANISM: artificial sequences
<220> FEATURE:
<221> NAME/KEY: SOURCE
<222> LOCATION: 1..27
<223> OTHER INFORMATION: /mol_type="protein"

```
/note="Antigen-Binding protein CH2 domain"
/organism="artificial sequences"

<400> SEQUENCE: 34

Ala Pro Glu Leu Leu Gly Gly Pro Ser Val Phe Ile Phe Pro Pro Lys
1               5                   10                  15

Pro Lys Asp Val Leu Ser Ile Ser Gly Arg Pro
            20                  25

<210> SEQ ID NO 35
<211> LENGTH: 12
<212> TYPE: PRT
<213> ORGANISM: artificial sequences
<220> FEATURE:
<221> NAME/KEY: SOURCE
<222> LOCATION: 1..12
<223> OTHER INFORMATION: /mol_type="protein"
      /note="Antigen-Binding protein CH3 domain"
      /organism="artificial sequences"

<400> SEQUENCE: 35

Gly Gln Thr Arg Glu Pro Gln Val Tyr Thr Leu Ala
1               5                   10

<210> SEQ ID NO 36
<211> LENGTH: 18
<212> TYPE: PRT
<213> ORGANISM: artificial sequences
<220> FEATURE:
<221> NAME/KEY: SOURCE
<222> LOCATION: 1..18
<223> OTHER INFORMATION: /mol_type="protein"
      /note="Antigen-Binding protein CH3 domain"
      /organism="artificial sequences"
<220> FEATURE:
<221> NAME/KEY: MOD_RES
<222> LOCATION: 14
<223> OTHER INFORMATION: Xaa can be any naturally occuring amino acid

<400> SEQUENCE: 36

Gly Gln Thr Arg Glu Pro Gln Val Tyr Thr Leu Ala Pro Xaa Arg Leu
1               5                   10                  15

Glu Leu

<210> SEQ ID NO 37
<211> LENGTH: 18
<212> TYPE: PRT
<213> ORGANISM: artificial sequences
<220> FEATURE:
<221> NAME/KEY: SOURCE
<222> LOCATION: 1..18
<223> OTHER INFORMATION: /mol_type="protein"
      /note="Antigen-Binding protein CH3 domain"
      /organism="artificial sequences"

<400> SEQUENCE: 37

Gly Gln Pro Arg Glu Pro Gln Val Tyr Thr Leu Pro Pro Ser Arg Asp
1               5                   10                  15

Glu Leu

<210> SEQ ID NO 38
<211> LENGTH: 18
<212> TYPE: PRT
<213> ORGANISM: artificial sequences
<220> FEATURE:
<221> NAME/KEY: SOURCE
<222> LOCATION: 1..18
<223> OTHER INFORMATION: /mol_type="protein"
```

/note="Antigen-Binding protein CH3 domain"
/organism="artificial sequences"

<400> SEQUENCE: 38

Gly Gln Pro Arg Glu Pro Gln Val Tyr Thr Leu Pro Pro Ser Arg Glu
1               5                   10                  15

Glu Met

<210> SEQ ID NO 39
<211> LENGTH: 18
<212> TYPE: PRT
<213> ORGANISM: artificial sequences
<220> FEATURE:
<221> NAME/KEY: SOURCE
<222> LOCATION: 1..18
<223> OTHER INFORMATION: /mol_type="protein"
      /note="Antigen-Binding protein CH3 domain"
      /organism="artificial sequences"

<400> SEQUENCE: 39

Gly Gln Pro Arg Glu Pro Gln Val Tyr Thr Leu Pro Pro Ser Gln Glu
1               5                   10                  15

Glu Met

<210> SEQ ID NO 40
<211> LENGTH: 12
<212> TYPE: PRT
<213> ORGANISM: artificial sequences
<220> FEATURE:
<221> NAME/KEY: SOURCE
<222> LOCATION: 1..12
<223> OTHER INFORMATION: /mol_type="protein"
      /note="Antigen-Binding protein Hinge domain"
      /organism="artificial sequences"

<400> SEQUENCE: 40

Gly Thr Asn Glu Val Cys Lys Cys Pro Lys Cys Pro
1               5                   10

<210> SEQ ID NO 41
<211> LENGTH: 35
<212> TYPE: PRT
<213> ORGANISM: artificial sequences
<220> FEATURE:
<221> NAME/KEY: SOURCE
<222> LOCATION: 1..35
<223> OTHER INFORMATION: /mol_type="protein"
      /note="Antigen-Binding protein Hinge domain"
      /organism="artificial sequences"

<400> SEQUENCE: 41

Glu Pro Lys Ile Pro Gln Pro Gln Pro Lys Pro Gln Pro Gln Pro Gln
1               5                   10                  15

Pro Gln Pro Lys Pro Gln Pro Lys Pro Glu Pro Glu Cys Thr Cys Pro
                20                  25                  30

Lys Cys Pro
        35